United States Patent [19]
McCoy et al.

[11] Patent Number: 6,143,524
[45] Date of Patent: *Nov. 7, 2000

[54] PEPTIDE AND PROTEIN FUSIONS TO THIOREDOXIN, THIOREDOXIN-LIKE MOLECULES, AND MODIFIED THIOREDOXIN-LIKE MOLECULES

[75] Inventors: John McCoy, Reading; Elizabeth DiBlasio-Smith, Tyngsboro; Kathleen Grant, Salem; Edward R. LaVallie, Tewksbury, all of Mass.

[73] Assignee: Genetics Institute, Inc., Cambridge, Mass.

[*] Notice: This patent is subject to a terminal disclaimer.

[21] Appl. No.: 08/810,436

[22] Filed: Mar. 4, 1997

Related U.S. Application Data

[60] Division of application No. 08/165,301, Dec. 10, 1993, Pat. No. 5,646,016, which is a continuation-in-part of application No. 07/921,848, Jul. 28, 1992, Pat. No. 5,292,646, which is a continuation-in-part of application No. 07/745,382, Aug. 14, 1991, Pat. No. 5,270,181, which is a continuation-in-part of application No. 07/652,531, Feb. 6, 1991, abandoned.

[51] Int. Cl.$^7$ .......................... C12N 15/24; C12N 15/63; C07K 14/54

[52] U.S. Cl. ..................... 435/69.7; 435/172.3; 435/325; 435/252.3; 435/320.1; 536/23.4; 935/47; 530/351

[58] Field of Search .................. 435/69.7, 172.3, 435/325, 252.3, 320.1; 536/23.4; 935/47; 530/351

[56] References Cited

U.S. PATENT DOCUMENTS 5,115,102  5/1992  Haymore et al. ................ 530/399
5,646,016  7/1997  McCoy et al. .................. 435/69.7

FOREIGN PATENT DOCUMENTS

A-12709/88       3/1987  Australia .
A2 0 035 384     2/1981  European Pat. Off. .
PCT/US90/04739   8/1990  WIPO .
WO A1 92/13955   8/1992  WIPO .

OTHER PUBLICATIONS

Hochuli et al., Bio/Technology 6:1321–1325 (Nov. 1988).
Wakasugi et al., Proc. Natl. Acad. Sci. U.S.A. 87:8282–8286 (1990).
Bardwell et al., Cell 67:581–589 (1991).
Bennett et al., Nature 334:268–270 (1988).
Mazzarella et al., J. Biol. Chem. 265:1094–1101 (1990).
LaVallie et al., Bio/Technology 11:187–193 (1993).
Ellis et al., Biochemistry 31:4882–91 (1992).
Murby et al., Biotech. and Applied Biochem. 14:336–346 (1991).
Kamo et al., Eur. J. Biochem. 182:315–322 (1989).
Boado et al., Biochem. and Biophys. Res. Comm. 155(3):1287–1304 (1988).
Pihlajaniemi et al., EMBO J. 6(3):643–649 (1987).
Hellinga, et al., J. Mol. Biol. 222:786–803 (1991).

Primary Examiner—Stephen Walsh
Assistant Examiner—Prema Mertz
Attorney, Agent, or Firm—Steven R. Lazar

[57] ABSTRACT

Provided is a fusion molecule comprising a DNA sequence encoding a thioredoxin-like protein fused to a DNA sequence encoding a second peptide or protein. The peptide or protein may be fused to the amino terminus of the thioredoxin-like molecule, the carboxyl terminus of the thioredoxin-like molecule, or within the thioredoxin-like molecule, for example at the active-site loop of the molecule. The fusion molecule may be modified to introduce one or more metal-binding/chelating amino-acid residues to aid in purification. Expression of this fusion molecule under the control of a regulatory sequence capable of directing its expression in a desired host cell, produces high levels of stable and soluble fusion protein. The fusion protein, located in the bacterial cytoplasm, may be selectively released from the cell by osmotic shock or freeze/thaw procedures. It may be optionally cleaved to liberate the soluble, correctly folded heterologous protein from the thioredoxin-like portion.

7 Claims, 12 Drawing Sheets

FIG. 1 pALtrxA/EK/IL11ΔPro-581
SEQ ID NO:13 and SEQ ID NO:14

GACGAAAGGG CCTCGTGATA CGCCTATTTT TATAGGTTAA
TGTCATGATA ATAATGGTTT CTTAGACGTC AGGTGGCACT
TTTCGGGGAA ATGTGCGCGG AACCCCTATT TGTTTATTTT
TCTAAATACA TTCAAATATG TATCCGCTCA TGAGACAATA
ACCCTGATAA ATGCTTCAAT AATATTGAAA AAGGAAGAGT
ATGAGTATTC AACATTTCCG TGTCGCCCTT ATTCCCTTTT
TTGCGGCATT TTGCCTTCCT GTTTTGCTC ACCCAGAAAC
GCTGGTGAAA GTAAAGATG CTGAAGATCA GTTGGGTGCA
CGAGTGGGTT ACATCGAACT GGATCTCAAC AGCGGTAAGA
TCCTTGAGAG TTTTCGCCCC GAAGAACGTT TTCCAATGAT
GAGCACTTTT AAAGTTCTGC TATGTGGCGC GGTATTATCC
CGTATTGACG CCGGGCAAGA GCAACTCGGT CGCCGCATAC
ACTATTCTCA GAATGACTTG GTTGAGTACT CACCAGTCAC
AGAAAAGCAT CTTACGGATG GCATGACAGT AAGAGAATTA
TGCAGTGCTG CCATAACCAT GAGTGATAAC ACTGCGGCCA
ACTTACTTCT GACAACGATC GGAGGACCGA AGGAGCTAAC
CGCTTTTTTG CACAACATGG GGGATCATGT AACTCGCCTT
GATCGTTGGG AACCGGAGCT GAATGAAGCC ATACCAAACG
ACGAGCGTGA CACCACGATG CCTGTAGCAA TGGCAACAAC
GTTGCGCAAA CTATTAACTG GCGAACTACT TACTCTAGCT
TCCCGGCAAC AATTAATAGA CTGGATGGAG GCGGATAAAG
TTGCAGGACC ACTTCTGCGC TCGGCCCTTC CGGCTGGCTG
GTTTATTGCT GATAAATCTG GAGCCGGTGA GCGTGGGTCT
CGCGGTATCA TTGCAGCACT GGGGCCAGAT GGTAAGCCCT
CCCGTATCGT AGTTATCTAC ACGACGGGGA GTCAGGCAAC
TATGGATGAA CGAAATAGAC AGATCGCTGA GATAGGTGCC
TCACTGATTA AGCATTGGTA ACTGTCAGAC CAAGTTTACT
CATATATACT TTAGATTGAT TTAAAACTTC ATTTTTAATT
TAAAAGGATC TAGGTGAAGA TCCTTTTTGA TAATCTCATG
ACCAAAATCC CTTAACGTGA GTTTTCGTTC CACTGAGCGT
CAGACCCCGT AGAAAAGATC AAAGGATCTT CTTGAGATCC

FIG. 1A

```
TTTTTTTCTG CGCGTAATCT GCTGCTTGCA AACAAAAAAA
CCACCGCTAC CAGCGGTGGT TTGTTTGCCG GATCAAGAGC
TACCAACTCT TTTTCCGAAG GTAACTGGCT TCAGCAGAGC
GCAGATACCA AATACTGTCC TTCTAGTGTA GCCGTAGTTA
GGCCACCACT TCAAGAACTC TGTAGCACCG CCTACATACC
TCGCTCTGCT AATCCTGTTA CCAGTGGCTG CTGCCAGTGG
CGATAAGTCG TGTCTTACCG GGTTGGACTC AAGACGATAG
TTACCGGATA AGGCGCAGCG GTCGGGCTGA ACGGGGGGTT
CGTGCACACA GCCCAGCTTG GAGCGAACGA CCTACACCGA
ACTGAGATAC CTACAGCGTG AGCATTGAGA AAGCGCCACG
CTTCCCGAAG GGAGAAAGGC GGACAGGTAT CCGGTAAGCG
GCAGGGTCGG AACAGGAGAG CGCACGAGGG AGCTTCCAGG
GGGAAACGCC TGGTATCTTT ATAGTCCTGT CGGGTTTCGC
CACCTCTGAC TTGAGCGTCG ATTTTGTGA TGCTCGTCAG
GGGGGCGGAG CCTATGGAAA AACGCCAGCA ACGCGGCCTT
TTTACGGTTC CTGGCCTTTT GCTGGCCTTT TGCTCACATG
TTCTTTCCTG CGTTATCCCC TGATTCTGTG GATAACCGTA
TTACCGCCTT TGAGTGAGCT GATACCGCTC GCCGCAGCCG
AACGACCGAG CGCAGCGAGT CAGTGAGCGA GGAAGCGGAA
GAGCGCCCAA TACGCAAACC GCCTCTCCCC GCGCGTTGGC
CGATTCATTA ATGCAGAATT GATCTCTCAC CTACCAAACA
ATGCCCCCCT GCAAAAAATA AATTCATATA AAAACATAC
AGATAACCAT CTGCGGTGAT AAATTATCTC TGGCGGTGTT
GACATAAATA CCACTGGCGG TGATACTGAG CACATCAGCA
GGACGCACTG ACCACCATGA ATTCAAGAAG GAGATATACA
```

| T | ATG | AGC | GAT | AAA | ATT | ATT | CAC | CTG | ACT | GAC | GAC | |
| | Met | Ser | Asp | Lys | Ile | Ile | His | Leu | Thr | Asp | Asp | |
| | 1 | | | 5 | | | | | | 10 | | |

| AGT | TTT | GAC | ACG | GAT | GTA | CTC | AAA | GCG | GAC | GGG | 2307 |
| Ser | Phe | Asp | Thr | Asp | Val | Leu | Lys | Ala | Asp | Gly | |
| | | | 15 | | | | | | 20 | | |

| GCG | ATC | CTC | GTC | GAT | TTC | TGG | GCA | GAG | TGG | TGC | 2340 |
| Ala | Ile | Leu | Val | Asp | Phe | Trp | Ala | Glu | Trp | Cys | |
| | | | 25 | | | | | 30 | | | |

FIG. 1B

| | | | | | | | | | | |
|---|---|---|---|---|---|---|---|---|---|---|
| GGT | CCG | TGC | AAA | ATG | ATC | GCC | CCG | ATT | CTG | GAT | 2373 |
| Gly | Pro | Cys | Lys | Met | Ile | Ala | Pro | Ile | Leu | Asp |
| | 35 | | | | 40 | | | | | |

GAA ATC GCT GAC GAA TAT CAG GGC AAA CTG ACC    2406
Glu Ile Ala Asp Glu Tyr Gln Gly Lys Leu Thr
 45              50                    55

GTT GCA AAA CTG AAC ATC GAT CAA AAC CCT GGC    2439
Val Ala Lys Leu Asn Ile Asp Gln Asn Pro Gly
             60                 65

ACT GCG CCG AAA TAT GGC ATC CGT GGT ATC CCG    2472
Thr Ala Pro Lys Tyr Gly Ile Arg Gly Ile Pro
         70                    75

ACT CTG CTG CTG TTC AAA AAC GGT GAA GTG GCG    2505
Thr Leu Leu Leu Phe Lys Asn Gly Glu Val Ala
             80                85

GCA ACC AAA GTG GGT GCA CTG TCT AAA GGT CAG    2538
Ala Thr Lys Val Gly Ala Leu Ser Lys Gly Gln
         90                    95

TTG AAA GAG TTC CTC GAC GCT AAC CTG GCC GGT    2571
Leu Lys Glu Phe Leu Asp Ala Asn Leu Ala Gly
100                 105                 110

TCT GGT TCT GGT GAT GAC GAT GAC AAA GGT CCA    2604
Ser Gly Ser Gly Asp Asp Asp Asp Lys Gly Pro
                 115                 120

CCA CCA GGT CCA CCT CGA GTT TCC CCA GAC CCT    2637
Pro Pro Gly Pro Pro Arg Val Ser Pro Asp Pro
             125                 130

CGG GCC GAG CTG GAC AGC ACC GTG CTC CTG ACC    2670
Arg Ala Glu Leu Asp Ser Thr Val Leu Leu Thr
         135                    140

CGC TCT CTC CTG GCG GAC ACG CGG CAG CTG GCT    2703
Arg Ser Leu Leu Ala Asp Thr Arg Gln Leu Ala
     145                    150

GCA CAG CTG AGG GAC AAA TTC CCA GCT GAC GGG    2736
Ala Gln Leu Arg Asp Lys Phe Pro Ala Asp Gly
155                 160                 165

FIG. 1C

| | | | | | | | | | | |
|---|---|---|---|---|---|---|---|---|---|---|
| GAC | CAC | AAC | CTG | GAT | TCC | CTG | CCC | ACC | CTG | GCC | 2769
| Asp | His | Asn | Leu | Asp | Ser | Leu | Pro | Thr | Leu | Ala |
| | | | | 170 | | | | | 175 | |

| ATG | AGT | GCG | GGG | GCA | CTG | GGA | GCT | CTA | CAG | CTC | 2802
| Met | Ser | Ala | Gly | Ala | Leu | Gly | Ala | Leu | Gln | Leu |
| | | | 180 | | | | | 185 | | |

| CCA | GGT | GTG | CTG | ACA | AGG | CTG | CGA | GCG | GAC | CTA | 2835
| Pro | Gly | Val | Leu | Thr | Arg | Leu | Arg | Ala | Asp | Leu |
| | | | 190 | | | | 195 | | | |

| CTG | TCC | TAC | CTG | CGG | CAC | GTG | CAG | TGG | CTG | CGC | 2868
| Leu | Ser | Tyr | Leu | Arg | His | Val | Gln | Trp | Leu | Arg |
| | | 200 | | | | 205 | | | | |

| CGG | GCA | GGT | GGC | TCT | TCC | CTG | AAG | ACC | CTG | GAG | 2901    Arg
| Ala | Gly | Gly | Ser | Ser | Leu | Lys | Thr | Leu | Glu | |
| 210 | | | | | 215 | | | | 220 | |

| CCC | GAG | CTG | GGC | ACC | CTG | CAG | GCC | CGA | CTG | GAC | 2934
| Pro | Glu | Leu | Gly | Thr | Leu | Gln | Ala | Arg | Leu | Asp |
| | | | | 225 | | | | | 230 | |

| CGG | CTG | CTG | CGC | CGG | CTG | CAG | CTC | CTG | ATG | TCC | 2967
| Arg | Leu | Leu | Arg | Arg | Leu | Gln | Leu | Leu | Met | Ser |
| | | | | 235 | | | | | 240 | |

| CGC | CTG | GCC | CTG | CCC | CAG | CCA | CCC | CCG | GAC | CCG | 3000    Arg
| Leu | Ala | Leu | Pro | Gln | Pro | Pro | Pro | Asp | Pro | |
| | | | 245 | | | | | 250 | | |

| CCG | GCG | CCC | CCG | CTG | GCG | CCC | CCC | TCC | TCA | GCC | 3033
| Pro | Ala | Pro | Pro | Leu | Ala | Pro | Pro | Ser | Ser | Ala |
| | | | 255 | | | | | 260 | | |

| TGG | GGG | GGC | ATC | AGG | GCC | GCC | CAC | GCC | ATC | CTG | 3066
| Trp | Gly | Gly | Ile | Arg | Ala | Ala | His | Ala | Ile | Leu |
| 265 | | | | | 270 | | | | | 275 |

| GGG | GGG | CTG | CAC | CTG | ACA | CTT | GAC | TGG | GCC | GTG | 3099
| Gly | GLy | Leu | His | Leu | Thr | Leu | Asp | Trp | Ala | Val |
| | | | | 280 | | | | | 285 | |

| AGG | GGA | CTG | CTG | CTG | CTG | AAG | ACT | CGG | CTG | TGA | 3132
| Arg | Gly | Leu | Leu | Leu | Leu | Lys | Thr | Arg | Leu | |
| | | | | 290 | | | | | 295 | |

FIG. 1D

| | | | | |
|---|---|---|---|---|
| AAGCTTATCG | ATACCGTCGA | CCTGCAGTAA | TCGTACAGGG | 3172 |
| TAGTACAAAT | AAAAAAGGCA | CGTCAGATGA | CGTGCCTTTT | 3212 |
| TTCTTGTGAG | CAGTAAGCTT | GGCACTGGCC | GTCGTTTTAC | 3252 |
| AACGTCGTGA | CTGGGAAAAC | CCTGGCGTTA | CCCAACTTAA | 3292 |
| TCGCCTTGCA | GCACATCCCC | CTTTCGCCAG | CTGGCGTAAT | 3332 |
| AGCGAAGAGG | CCCGCACCGA | TCGCCTTCC | CAACAGTTGC | 3372 |
| GCAGCCTGAA | TGGCGAATGG | CGCCTGATGC | GGTATTTTCT | 3412 |
| CCTTACGCAT | CTGTGCGGTA | TTTCACACCG | CATATATGGT | 3452 |
| GCACTCTCAG | TACAATCTGC | TCTGATGCCG | CATAGTTAAG | 3492 |
| CCAGCCCCGA | CACCCGCCAA | CACCCGCTGA | CGCGCCCTGA | 3532 |
| CGGGCTTGTC | TGCTCCCGGC | ATCCGCTTAC | AGACAAGCTG | 3572 |
| TGACCGTCTC | CGGGAGCTGC | ATGTGTCAGA | GGTTTTCACC | 3612 |
| GTCATCACCG | AAACGCGCGA | | | 3632 |

FIG. 2

MIP-1α

SEQ ID NO:15 and SEQ ID NO:16

| GCA | CCA | CTT | GCT | GCT | GAC | ACG | CCG | ACC | GCC | TGC | TGC | 36 |
|-----|-----|-----|-----|-----|-----|-----|-----|-----|-----|-----|-----|-----|
| Ala | Pro | Leu | Ala | Ala | Asp | Thr | Pro | Thr | Ala | Cys | Cys | |
| 1 | | | | 5 | | | | | 10 | | | |

| TTC | AGC | TAC | ACC | TCC | CGA | CAG | ATT | CCA | CAG | AAT | TTC | 72 |
|-----|-----|-----|-----|-----|-----|-----|-----|-----|-----|-----|-----|-----|
| Phe | Ser | Tyr | Thr | Ser | Arg | Gln | Ile | Pro | Gln | Asn | Phe | |
| | | 15 | | | | | 20 | | | | | |

| ATA | GCT | GAC | TAC | TTT | GAG | ACG | AGC | AGC | CAG | TGC | TCC | 108 |
|-----|-----|-----|-----|-----|-----|-----|-----|-----|-----|-----|-----|-----|
| Ile | Ala | Asp | Tyr | Phe | Glu | Thr | Ser | Ser | Gln | Cys | Ser | |
| 25 | | | | | 30 | | | | | 35 | | |

| AAG | CCC | AGT | GTC | ATC | TTC | CTA | ACC | AAG | AGA | GGC | CGG | 144 |
|-----|-----|-----|-----|-----|-----|-----|-----|-----|-----|-----|-----|-----|
| Lys | Pro | Ser | Val | Ile | Phe | Leu | Thr | Lys | Arg | Gly | Arg | |
| | | | 40 | | | | | 45 | | | | |

| CAG | GTC | TGT | GCT | GAC | CCC | AGT | GAG | GAG | TGG | GTC | CAG | 180 |
|-----|-----|-----|-----|-----|-----|-----|-----|-----|-----|-----|-----|-----|
| Gln | Val | Cys | Ala | Asp | Pro | Ser | Glu | Glu | Trp | Val | Gln | |
| | 50 | | | | | 55 | | | | | 60 | |

| AAA | TAC | GTC | AGT | GAC | CTG | GAG | CTG | AGT | GCC | TAA | | 213 |
|-----|-----|-----|-----|-----|-----|-----|-----|-----|-----|-----|-----|-----|
| Lys | Thr | Val | Ser | Asp | Leu | Glu | Leu | Ser | Ala | | | |
| | | | | 65 | | | | | 70 | | | |

FIG. 3

BMP-2

SEQ ID NO:17 and SEQ ID NO:18

| CAA | GCT | AAA | CAT | AAA | CAA | CGT | AAA | CGT | CTG | AAA | TCT | 36 |
|---|---|---|---|---|---|---|---|---|---|---|---|---|
| Gln | Ala | Lys | His | Lys | Gln | Arg | Lys | Arg | Leu | Lys | Ser | |
| 1 | | | | 5 | | | | | 10 | | | |

| AGC | TGT | AAG | AGA | CAC | CCT | TTG | TAC | GTG | GAC | TTC | AGT | 72 |
|---|---|---|---|---|---|---|---|---|---|---|---|---|
| Ser | Cys | Lys | Arg | His | Pro | Leu | Tyr | Val | Asp | Phe | Ser | |
| | | 15 | | | | | 20 | | | | | |

| GAC | GTG | GGG | TGG | AAT | GAC | TGG | ATT | GTG | GCT | CCC | CCG | 108 |
|---|---|---|---|---|---|---|---|---|---|---|---|---|
| Asp | Val | Gly | Trp | Asn | Asp | Trp | Ile | Val | Ala | Pro | Pro | |
| 25 | | | | | 30 | | | | | 35 | | |

| GGG | TAT | CAC | GCC | TTT | TAC | TGC | CAC | GGA | GAA | TGC | CCT | 144 |
|---|---|---|---|---|---|---|---|---|---|---|---|---|
| Gly | Tyr | His | Ala | Phe | Tyr | Cys | His | Gly | Glu | Cys | Pro | |
| | | | 40 | | | | | 45 | | | | |

| TTT | CCT | CTG | GCT | GAT | CAT | CTG | AAC | TCC | ACT | AAT | CAT | 180 |
|---|---|---|---|---|---|---|---|---|---|---|---|---|
| Phe | Pro | Leu | Ala | Asp | His | Leu | Asn | Ser | Thr | Asn | His | |
| | 50 | | | | | 55 | | | | | 60 | |

| GCC | ATT | GTT | CAG | ACG | TTG | GTC | AAC | TCT | GTT | AAC | TCT | 216 |
|---|---|---|---|---|---|---|---|---|---|---|---|---|
| Ala | Ile | Val | Gln | Thr | Leu | Val | Asn | Ser | Val | Asn | Ser | |
| | | | | 65 | | | | | 70 | | | |

| AAG | ATT | CCT | AAG | GCA | TGC | TGT | GTC | CCG | ACA | GAA | CTC | 252 |
|---|---|---|---|---|---|---|---|---|---|---|---|---|
| Lys | Ile | Pro | Lys | Ala | Cys | Cys | Val | Pro | Thr | Glu | Leu | |
| | | 75 | | | | | 80 | | | | | |

| AGT | GCT | ATC | TCG | ATG | CTG | TAC | CTT | GAC | GAG | AAT | GAA | 288 |
|---|---|---|---|---|---|---|---|---|---|---|---|---|
| Ser | Ala | Ile | Ser | Met | Leu | Tyr | Leu | Asp | Glu | Asn | Glu | |
| 85 | | | | | 90 | | | | | 95 | | |

| AAG | GTT | GTA | TTA | AAG | AAC | TAT | CAG | GAC | ATG | GTT | GTG | 324 |
|---|---|---|---|---|---|---|---|---|---|---|---|---|
| Lys | Val | Val | Leu | Lys | Asn | Tyr | Gln | Asp | Met | Val | Val | |
| | | | 100 | | | | | 105 | | | | |

| GAG | GGT | TGT | GGG | TGT | CGC | TAG | | | | | | 345 |
|---|---|---|---|---|---|---|---|---|---|---|---|---|
| Glu | Gly | Cys | Gly | Cys | Arg | | | | | | | |
| | 110 | | | | | | | | | | | |

FIG. 4

INSERTION OF AN ENTEROKINASE SITE INTO
THE ACTIVE-SITE LOOP OF E.COLI THIOREDOXIN (trxA)

```
                           RsrII
                             |
                ....GAGTGGTGCGGTCCGTGCAAAATG....
trxA active     ---------------------------
site loop       ....CTCACCACGCCAGGCACGTTTTAC....

....E   W   C   G   P   C   K   M  ....
                     31                              38
```

```
                ....GAGTGGTGCG         GTCCGTGCAAAATG....
RsrII cut       ----------             --------------
                ....CTCACCACGCCAG          GCACGTTTTAC....

....E  W  C  G           P  C  K  M ....
                     31                                 38
```

Enterokinase site
(13 residues)

```
        gtcactccGACTACAAAGACGACGACGACAAAgcttctg
        ---------------------------------------
        tgaggCTGATGTTTCTGCTGCTGCTGTTTcgaagaccag ....H  S  D  Y  K  D  D  D  D  K  A  S  G...
                                    ^
                                    ^
                                    ^
                                cleavage site
```

FIG. 5

RANDOM PEPTIDE INSERTIONS INTO THE ACTIVE-SITE
LOOP OF E.COLI THIOREDOXIN (trxA)

```
                              RsrII
                               |
                    ....GAGTGGTGCGGTCCGTGCAAAATG....
trxA active         ------------------------
site loop           ....CTCACCACGCCAGGCACGTTTTAC....

....E  W  C  G  P  C  K  M ....
                        31               38
```

```
              ....GAGTGGTGCG        GTCCGTGCAAAATG....
RsrII cut     ----------            ----------
              ....CTCACCACGCCAG     GCACGTTTTAC....

....E  W  C  G         P  C  K  M ....
                  31                          38
```

```
                  (AvaII)              AvaII
          5'        |                    |              3'
              GACTGACTGGTCCG...(N36)...GGTCCTCAGTCAGTCAG
oligos    -----------------------------------------
                                       CCAGGAGTCAGTCAGTC
                           3'                          5'
```

```
random            GTCCG...(N36)...G
duplex            ---------------
                  GC...(N36)...CCAG
``` insertion into trxA active site loop

```
              ....GAGTGGTGCGGTCCG...(N36)...GGTCCGTGCAAAATG....
              ---------------------------------------
              ....CTCACCACGCCAGGC...(N36)...CCAGGCACGTTTTAC....

SEQ ID NO:19 and SEQ ID NO:20

|  |  |  |  |  | 5 |  |  |  |  | 10 |  |  |  |
|---|---|---|---|---|---|---|---|---|---|---|---|---|---|
| ATG | GCT | CCA | GTA | CCT | CCA | GGT | GAA | GAT | TCT | AAA | GAT | GTA | 39 |
| Met | Ala | Pro | Val | Pro | Pro | Gly | Glu | Asp | Ser | Lys | Asp | Val |  |

```
                    15                      20                      25
GCC GCC CCA CAC AGA CAG CCA CTC ACC TCT TCA GAA CGA          78
Ala Ala Pro His Arg Gln Pro Leu Thr Ser Ser Glu Arg 30                      35
ATT GAC AAA CAA ATT CGG TAC ATC CTC GAC GGC ATC TCA          117
Ile Asp Lys Gln Ile Arg Tyr Ile Leu Asp Gly Ile Ser 40                          45                      50
GCC CTG AGA AAG GAG ACA TGT AAC AAG AGT AAC ATG TGT          156
Ala Leu Arg Lys Glu Thr Cys Asn Lys Ser Asn Met Cys 55                      60                      65
GAA AGC AGC AAA GAG GCA CTG GCA GAA AAC AAC CTG AAC          195
Glu Ser Ser Lys Glu Ala Leu Ala Glu Asn Asn Leu Asn 70                      75
CTT CCA AAG ATG GCT GAA AAA GAT GGA TGC TTC CAA TCT          234
Leu Pro Lys Met Ala Glu Lys Asp Gly Cys Phe Gln Ser 80                      85                      90
GGA TTC AAT GAG GAG ACT TGC CTG GTG AAA ATC ATC ACT          273
Gly Phe Asn Glu Glu Thr Cys Leu Val Lys Ile Ile Thr 95                     100
GGT CTT TTG GAG TTT GAG GTA TAC CTA GAG TAC CTC CAG          312
Gly Leu Leu Glu Phe Glu Val Tyr Leu Glu Thr Leu Gln 105                     110                     115
AAC AGA TTT GAG AGT AGT GAG GAA CAA GCC AGA GCT GTG          351
Asn Arg Phe Glu Ser Ser Glu Glu Gln Ala Arg Ala Val
```

FIG. 6A

```
              120                           125                           130
    CAG ATG AGT ACA AAA GTC CTG ATC CAG TTC CTG CAG AAA     390
    Gln Met Ser Thr Lys Val Leu Ile Gln Phe Leu Gln Lys 135                       140
    AAG GCA AAG AAT CTA GAT GCA ATA ACC ACC CCT GAC CCA     429
    Lys Ala Lys Asn Leu Asp Ala Ile Thr Thr Pro Asp Pro 145                       150                       155
    ACC ACA AAT GCC AGC CTG CTG ACG AAG CTG CAG GCA CAG     468
    Thr Thr Asn Ala Ser Leu Leu Thr Lys Leu Gln Ala Gln 160                       165
    AAC CAG TGG CTG CAG GAC ATG ACA ACT CAT CTC ATT CTG     507
    Asn Gln Trp Leu Gln Asp Met Thr Thr His Leu Ile Leu 170                       175                       180
    CGC AGC TTT AAG GAG TTC CTG CAG TCC AGC CTG AGG GCT     546
    Arg Ser Phe Lys Glu Phe Leu Gln Ser Ser Leu Arg Ala

185
    CTT CGG CAA ATG TAG                                      561
    Leu Arg Gln Met  *
```

FIG. 7
(SEQ ID NO: 23)
(SEQ ID NO: 24)

```
  1 GAAGAAGTTT CTGAATATTG TAGCCACATG ATTGGGAGTG GACACCTGCA
 51 GTCTCTGCAG CGGCTGATTG ACAGTCAGAT GGAGACCTCG TGCCAAATTA
101 CATTTGAGTT TGTAGACCAG GAACAGTTGA AAGATCCAGT GTGCTACCTT
151 AAGAAGGCAT TTCTCCTGGT ACAAGACATA ATGGAGGACA CCATGCGCTT
201 CAGAGATAAC ACCCCCAATG CCATCGCCAT TGTGCAGCTG CAGGAACTCT
251 CTTTGAGGCT GAAGAGCTGC TTCACCAAGG ATTATGAAGA GCATGACAAG
301 GCCTGCGTCC GAACTTTCTA TGAGACACCT CTCCAGTTGC TGGAGAAGGT
351 CAAGAATGTC TTTAATGAAA CAAAGAATCT CCTTGACAAG GACTGGAATA
401 TTTTCAGCAA GAACTGCAAC AACAGCTTTG CTGAATGCTC CAGCCAAGAT
451 GTGGTGACCA AGCCTGATTG CAACTGCCTG TACCCCAAAG CCATCCCTAG
501 CAGTGACCCG GCCTCTGTCT CCCCTCATCA GCCCCTCGCC CCTCCATGG
551 CCCCTGTGGC TGGCTTGACC TGGGAGGACT CTGAGGGAAC TGAGGGCAGC
601 TCCCTCTTGC CTGGTGAGCA GCCCCTGCAC ACAGTGGATC CAGGCAGTGC
651 CAAGCAGCGG CCACCCAGG
```

PEPTIDE AND PROTEIN FUSIONS TO THIOREDOXIN, THIOREDOXIN-LIKE MOLECULES, AND MODIFIED THIOREDOXIN-LIKE MOLECULES

CROSS-REFERENCE TO RELATED APPLICATIONS

This application is a divisional of application Ser. No. 08/165,301, filed Dec. 10, 1993, now U.S. Pat. No. 5,646, 016; which in turn is a continuation-in-part of U.S. Ser. No. 07/921,848, filed Jul. 28, 1992, and issued Mar. 8, 1994 as U.S. Pat. No. 5,292,646; which is a continuation-in-part of U.S. Ser. No. 07/745,382, filed Aug. 14, 1991 and issued Dec. 14, 1993 as U.S. Pat. No. 5,270,181; which is a continuation-in-part of U.S. Ser. No. 07/652,531, filed Feb. 6, 1991 and now abandoned.

The present invention relates generally to the production of fusion proteins in prokaryotic and eukaryotic cells. More specifically, the invention relates to the expression in host cells of recombinant fusion sequences comprising thioredoxin or thioredoxin-like sequences fused to sequences for selected heterologous peptides or proteins, and the use of such fusion molecules to increase the production, activity, stability or solubility of recombinant proteins and peptides. In addition, provided by the present invention are fusion proteins having, e.g., the thioredoxin, or thioredoxin-like, or other fusion partner, modified to include metal-binding/chelating sequences, especially useful during purification.

BACKGROUND OF THE INVENTION

Many peptides and proteins can be produced via recombinant means in a variety of expression systems, e.g., various strains of bacterial, fungal, mammalian or insect cells. However, when bacteria are used as host cells for heterologous gene expression, several problems frequently occur.

For example, heterologous genes encoding small peptides are often poorly expressed in bacteria. Because of their size, most small peptides are unable to adopt stable, soluble conformations and are subject to intracellular degradation by proteases and peptidases present in the host cell. Those small peptides which do manage to accumulate when directly produced in E. coli or other bacterial hosts are usually found in the insoluble or "inclusion body" fraction, an occurrence which renders them almost useless for screening purposes in biological or biochemical assays.

Moreover, even if small peptides are not produced in inclusion bodies, their production by recombinant means as candidates for new drugs or enzyme inhibitors encounters further problems. Even small peptides can adopt an enormous number of potential structures due to their high degree of conformational freedom. Thus a small peptide can have the "desired" amino-acid sequence and yet have very low activity in an assay because the "active" peptide conformation is only one of the many alternative structures it can adopt in free solution. This presents another difficulty encountered in producing small heterologous peptides recombinantly for effective research and therapeutic use.

Inclusion body formation is also frequently observed when the genes for heterologous is proteins are expressed in bacterial cells. These inclusion bodies usually require further manipulations in order to solubilize and refold the heterologous protein, with conditions determined empirically and with uncertainty in each case.

If these additional procedures are not successful, little to no protein retaining bioactivity can be recovered from the host cells. Moreover, these additional processes are often technically difficult and prohibitively expensive for practical production of recombinant proteins for therapeutic, diagnostic or other research uses.

To overcome these problems, the art has employed certain peptides or proteins as fusion "partners" with a desired heterologous peptide or protein, to enable the recombinant production and/or secretion of small peptides or larger proteins as fusion proteins in bacterial expression systems. Among such fusion partners are included LacZ and TrpE proteins, maltose-binding protein and glutathione-S-transferase[See, generally, Current Protocols in Molecular Biology, Vol. 2, suppl. 10, publ. John Wiley and Sons, New York, N.Y., pp. 16.4.1–16.8.1 (1990); and Smith et al., Gene 67:31–40 (1988)]. As another example, U.S. Pat. No. 4,801, 536 describes the fusion of a bacterial flagellin gene to a desired gene to enable the production of a heterologous protein in a bacterial cell and its secretion into the culture medium as a fusion protein.

However, often fusions of desired peptides or proteins to other proteins (i.e. fusion partners) at the amino- or carboxyl- termini of these fusion partner proteins have other potential disadvantages. Experience in E. coli has shown that a crucial factor in obtaining high levels of gene expression is the efficiency of translation initiation. Translation initiation in E. coli is very sensitive to the nucleotide sequence surrounding the initiating methionine codon of the desired heterologous peptide or protein sequence, although the rules governing this phenomenon are not clear. For this reason, fusions of sequences at the amino-terminus of many fusion partner proteins can affect expression levels in an unpredictable manner. In addition there are numerous amino- and carboxy-peptidases in E. coli which degrade amino or carboxyl-terminal peptide extensions to fusion partner proteins so that a number of the known fusion partners have a low success rate for producing stable fusion proteins.

The purification of proteins produced by recombinant expression systems is often a serious challenge. Certain purification schemes, e.g., such as that disclosed in Haymore et al., U.S. Pat. No. 5,115,102 (filed Jul. 21, 1989, issued May 19, 1992), require the introduction of metal-chelating amino acid sequences into the protein of interest at a position dictated by the secondary structure of that protein, e.g., by locating α-helix, β-strand, and β-hairpin regions in the protein's structure, and by introducing two selected histidine residues separated by 3, 2 or 1 amino acid residues, respectively, into one of these regions. The modifications confer an affinity on the protein for metal-chelate columns which can be used as a purification tool. Unfortunately the introduction of such modifications as taught by the method can destroy the biological activity of the protein of interest, e.g., particularly where the substitution is a non-conservative change which can alter a ligand binding site, an active site, or other functional sites, and/or destroy important tertiary structural relationships in the protein. Moreover, certain of the introduced changes could result in mis-folding of the protein of interest. It is important to give consideration to the location of these vital protein features when making such modifications. Since the Haymore et al approach teaches that metal chelating amino acids must be positioned very precisely with respect to each other within the same element of secondary structure, there are a limited number of places in any one protein that can be so modified, and this number of potential metal-chelating sites diminishes when the important functional regions of the protein are excluded. For instance, for those proteins having α-helical region(s)

which are limited to the active site or to the receptor binding site of the molecule, it would not be possible to successfully utilize that region for modification while retaining funtionality. Furthermore only chelating sites formed by residues positioned close together in the primary sequence were considered in this method; and no allowance was given to the possibility of generating metal-chelating sites using residues positioned in the primary sequence further apart than 9 residues. However it is possible that two residues distant from each other in the primary sequence of a protein could, in fact, be adjacent in the folded tertiary structure, and thus could potentially be suitable places for the introduction of metal-chelating amino-acids.

Thus although there is a continuing need for new and easier methods to produce homogeneous preparations of recombinant proteins for use in research, diagnostic and therapeutic applications, there are many problems, such as those outlined above, in modifying the sequence of the desired proteins for purification purposes. These problems can be avoided by utilizing a fusion protein approach in which the fusion partner protein has the ability to bind to an affinity matrix, and the desired protein is left unaltered. Many fusion partners currently used in the art possess no inherent properties that would facilitate purification. However, the present invention provides, inter alia, the modification of a fusion partner protein, e.g., thioredoxin, in such a way as to enable it to bind to a metal chelate affinity matrix, providing an additional convenient purification tool that can be used for fusion proteins. The technique is also applicable to other proteins, including other fusion partner proteins, and proteins which are not fusion protein constructs.

SUMMARY OF THE INVENTION

In one aspect, the present invention provides a fusion sequence comprising a thioredoxin-like protein sequence fused to a selected heterologous peptide or protein. The peptide or protein may be fused to the amino terminus of the thioredoxin-like sequence, the carboxyl terminus of the thioredoxin-like sequence, or within the thioredoxin-like sequence (e.g., within the active-site loop of thioredoxin). The fusion sequence according to this invention may optionally contain a linker peptide between the thioredoxin-like sequence and the selected peptide or protein. This linker provides, where needed, a selected cleavage site or a stretch of amino acids capable of preventing steric hindrance between the thioredoxin-like molecule and the selected peptide or protein. Further, the fusion sequence may optionally comprise thioredoxin-like sequences modified to have affinity for e.g., metal affinity matrices or resins, by introducing, via addition, deletion, or substitution, one or more specific metal-binding or metal-chelating amino acid residues into the thioredoxin-like sequence of the fusion protein. The terms "metal binding", "metal chelating" and "metal affinity" are used interchangeably throughout the specification, as are the terms "metal" and "metal ion." The locations of these metal binding amino acids, as either additions, deletions or substitutions are dictated by the surface accessibility and proximity of the metal binding amino acids to each other, as is evident, e.g., from the thioredoxin tertiary sequence, and without regard to their location within elements of secondary structure. The number of amino acids modified depends, in part, on the relative spatial location of "naturally occurring" metal-binding/chelating amino acids in the protein. That is, the protein may fortuitously already contain one or more metal binding amino acids. Those amino acids which participate in the metal-binding/chelating are collectively referred to as a "patch," and, for example, where these amino acids happen to all be histidine, the patch is referred to as a "histidine patch." The protein may contain one or more of such "patches" to thereby alter the protein's affinity for the metal as desired. The use of greater numbers of "patches" would increase the affinity. Moreover, the modifications may be introduced into DNA sequences encoding proteins per se, i.e., the invention is not limited to the modification of fusion proteins.

As another aspect, the present invention provides a DNA molecule encoding the fusion sequence defined above in association with, and under the control of, an expression control sequence capable of directing the expression of the fusion protein in a desired host cell.

Still a further aspect of the invention is a host cell transformed with, or having integrated into its genome, a DNA sequence comprising a thioredoxin-like DNA sequence fused to the DNA sequence of a selected heterologous peptide or protein. This fusion sequence is desirably under the control of an expression control sequence capable of directing the production of a fusion protein in the cell.

As yet another aspect, there is provided a novel method for increasing the production of soluble recombinant proteins. The method includes culturing under suitable conditions the above-described host cell to produce the fusion protein. The terms "expression" and "production" may be used interchangeably herein to encompass the expression of a gene to produce a protein or peptide.

In one embodiment of this method, if the resulting fusion protein is cytoplasmic, the cell can be lysed by conventional means to obtain the soluble fusion protein. More preferably in the case of cytoplasmic fusion proteins, the method includes releasing the fusion protein from the host cell by applying osmotic shock or freeze/thaw treatments to the cell. In this case the fusion protein is selectively released from the interior of the cell via the zones of adhesion that exist between the inner and outer membranes of *E. coli*. The fusion protein is then purified by conventional means. In still another embodiment, if a secretory leader is employed in the fusion protein construct, the fusion protein can be recovered from a periplasmic extract or from the cell culture medium. As yet a further step in the above methods, the desired protein can be cleaved from fusion with the thioredoxin-like protein by conventional means.

Still another aspect of the present invention provides a method for purification of the fusion proteins, comprising, e.g., thioredoxin-like sequences modified to have affinity for metal affinity resins by the introduction of one or more specific metal-binding or metal-chelating amino acid residues into the thioredoxin-like sequences, in which the modified fusion proteins are exposed to and bound to a metal affinity matrix, purified away from contaminants by e.g., washing with buffer, eluted selectively by exposure to solutions containing soluble metal chelating agents, such as imidazole or EDTA, or by a change in solution pH, and recovered as, e.g., a column eluate, or a supernatant following centrifugation, or as a filtrate.

Other aspects and advantages of the present invention will be apparent upon consideration of the following detailed description of preferred embodiments thereof.

SUMMARY OF THE DRAWINGS AND SEQ ID NOS.:25–29

FIG. 1 illustrates the DNA sequence of the expression plasmid pALtrxA/EK/IL11ΔPro-581 (SEQ ID NO:13) and the amino acid sequence for the fusion protein therein (SEQ ID NO:14), described in Example 1.

FIG. 2 illustrates the DNA sequence (SEQ ID NO:15) and amino acid sequence (SEQ ID NO:16) of the macrophage inhibitory protein-1α (MIP-1α) protein used in the construction of a thioredoxin fusion protein described in Example 3.

FIG. 3 illustrates the DNA sequence (SEQ ID NO:17) and amino acid sequence (SEQ ID NO:18) of the bone morphogenetic protein-2 (BMP-2) protein used in the construction of a thioredoxin fusion protein described in Example 4.

FIG. 4 is a schematic drawing illustrating the insertion of an enterokinase cleavage site into the active-site loop of *E. coli* thioredoxin (trxA) described in Example 12.

FIG. 5 is a schematic drawing illustrating random peptide insertions into the active-site loop of *E. coli* thioredoxin (trxA) described in Example 12.

FIG. 6 illustrates the DNA sequence (SEQ ID NO:19) and amino acid sequence (SEQ ID NO:20) of the human interleukin-6 (IL-6) protein used in the construction of a thioredoxin fusion protein described in Example 13.

FIG. 7 illustrates the DNA sequence (SEQ ID NO:23) and amino acid sequence (SEQ ID NO:24) of the M-CSF protein used in the construction of a thioredoxin fusion protein described in Example 14.

SEQ ID NOS:25 and 26 are a modified form of the thioredoxin portion (SEQ ID NO:13) of the DNA of FIG. 1 and the corresponding amino acid sequence for the modified thioredoxin protein encoded by this DNA. This modified form of thioredoxin incorporates three amino acid changes from wildtype, i.e. the nucleotides encoding the amino acid residues at positions 2, 31 and 63 have been changed to encode histidine residues, and certain nucleotides in the DNA were altered to reflect *E.coli* preferred codons. This form of thioredoxin is termed "histidine patch" thioredoxin, or hpTRX.

SEQ ID NOS:27 and 28 represent the modified form of the thioredoxin portion of the DNA of FIG. 1 and the corresponding amino acid sequence for the modified thioredoxin protein encoded by this DNA. This modified form of thioredoxin incorporates two amino acid changes from wildtype, i e., the nucleotides encoding the amino acid residues at positions 31 and 63 have been changed to encode histidine residues, and certain nucleotides in the DNA were altered to reflect *E.coli* preferred codons. This form of thioredoxin is termed "histidine patch 2" thioredoxin, or hp2TRX.

SEQ ID NO:29 illustrates the nucleotide sequence of the thioredoxin/IL-11 gene fusion expression plasmid pHPTrxF-EKIL11dp-781, which incorporates a modified thioredoxin gene containing the mutations S2H, E31H and Q63H. This modified thioredoxin has affinity to metal ions and is called "hispatch" thioredoxin.

DETAILED DESCRIPTION OF THE INVENTION

The methods and compositions of the present invention permit the production of large amounts of heterologous peptides or proteins in a stable, soluble form in certain host cells which normally produce limited amounts of such peptides or proteins. The present invention produces fusion proteins which retain the desirable characteristics of a thioredoxin-like protein (i.e., stability, solubility and a high level of synthesis). The invention also allows a small peptide insert into an internal region of the thioredoxin-like sequence (e.g., the active-site loop of thioredoxin) to be accessible on the surface of the molecule. These fusion proteins also permit a peptide or protein fused at the free ends of the thioredoxin-like protein to achieve its desired confirmation.

According to the present invention, the DNA sequence encoding a heterologous peptide or protein selected for expression in a recombinant system is desirably fused to a thioredoxin-like DNA sequence for expression in the host cell. A thioredoxin-like DNA sequence is defined herein as a DNA sequence encoding a protein or fragment of a protein characterized by an amino acid sequence having at least 30% homology with the amino acid sequence of *E. coli* thioredoxin (SEQ ID NO:22). Alternatively, a thioredoxin-like DNA sequence is defined herein as a DNA sequence encoding a protein or fragment of a protein characterized by a having a three dimensional structure substantially similar to that of human or *E. coli* thioredoxin (SEQ ID NO:22) and optionally by containing an active-site loop. The DNA sequence of glutaredoxin is an example of a thioredoxin-like DNA sequence which encodes a protein that exhibits such substantial similarity in three-dimensional confirmation and contains a Cys . . . Cys active site loop. The amino acid sequence of *E. coli* thioredoxin is described in H. Eklund et al., EMBO J. 3:1443–1449 (1984). The three-dimensional structure of *E. coli* thioredoxin is depicted in FIG. 2 of A. Holmgren, J. Biol. Chem. 264:13963–13966 (1989). In FIG. 1 below nucleotides 2242–2568 encompasses a DNA sequence encoding the *E. coli* thioredoxin protein [Lim et al., J. Bacteriol., 163:311–316 (1985)] (SEQ ID NO:21). A comparison of the three dimensional structures of *E. coli* thioredoxin and glutaredoxin is published in Xia, Protein Science I:310–321 (1992). These four publications are incorporated herein by reference for the purpose of providing information on thioredoxin-like proteins that is known to one of skill in the art.

As the primary example of a thioredoxin-like protein useful in this invention, *E. coli* thioredoxin (SEQ ID NO:21 and SEQ ID NO:22) has the following characteristics. *E. coli* thioredoxin is a small protein, only 11.7 kD), and can be produced to high levels (>10%, corresponding to a concentration of 15 μM if cells are lysed at 10 $A_{550}$/ml). The small size and capacity for a high level synthesis of the protein contributes to a high intracellular concentration. *E. coli* thioredoxin is further characterized by a very stable, tight structure which can minimize the effects on overall structural stability caused by fusion to the desired peptide or proteins.

The three dimensional structure of *E. coli* thioredoxin is known and contains several surface loops, including a distinctive Cys . . . Cys active-site loop between residues $Cys_{33}$ and $Cys_{36}$ which protrudes from the body of the protein. This Cys . . . Cys active-site loop is an identifiable, accessible surface loop region and is not involved in any interactions with the rest of the protein that contribute to overall structural stability. It is therefore a good candidate as a site for peptide insertions. Both the amino- and carboxyl-termini of *E. coli* thioredoxin are on the surface of the protein, and are readily accessible for fusions. Human thioredoxin, glutaredoxin and other thioredoxin-like molecules also contain this Cys . . . Cys active-site loop.

*E. coli* thioredoxin is also stable to proteases. Thus, *E. coli* thioredoxin may be desirable for use in *E. coli* expression systems, because as an *E. coli* protein it is characterized by stability to *E. coli* proteases. *E. coli* thioredoxin is also stable to heat up to 80° C. and to low pH.

Other thioredoxin-like proteins encoded by thioredoxin-like DNA sequences useful in this invention share homologous amino acid sequences, and similar physical and structural characteristics. Thus, DNA sequences encoding other thioredoxin-like proteins may be used in place of *E. coli* thioredoxin (SEQ ID NO:21 and SEQ ID NO:22) according to this invention. For example, the DNA sequence encoding other species' thioredoxin, e.g., human thioredoxin, have been employed by these inventors in the compositions and methods of this invention. Human thioredoxin has a three dimensional structure that is virtually superimposable on *E. coli's* three-dimensional structure, as determined by comparing the NMR structures of the two molecules. Human thioredoxin also contains an active-site loop structurally and functionally equivalent to the Cys . . . Cys active-site loop found in the *E. coil* protein. Human IL-11 fused in frame to the carboxyl terminus of human thioredoxin (i.e., a human thioredoxin/IL-11 fusion) exhibited the same expression characteristics as the *E. coli* thioredoxin/IL-11 fusion exemplified in Examples 1–2. Consequently, human thioredoxin is a thioredoxin-like molecule and can be used in place of or in addition to *E. coli* thioredoxin in the production of protein and small peptides in accordance with the method of this invention. Insertions into the human thioredoxin active-site loop and onto the amino terminus may be as well tolerated as those in *E. coli* thioredoxin.

Other thioredoxin-like sequences which may be employed in this invention include all or portions of the protein glutaredoxin and various species' homologs thereof. [A. Holmgren, cited above.] Although *E. coli* glutaredoxin and *E. coli* thioredoxin share less than 20% amino acid homology, the two proteins do have conformational and functional similarities [Eklund et al., EMBO J. 3:1443–1449 (1984)] and glutaredoxin contains an active-site loop structurally and functionally equivalent to the Cys . . . Cys active-site loop of *E. coli* thioredoxin. Glutaredoxin is therefore a thioredoxin-like molecule as herein defined.

The DNA sequence encoding protein disulfide isomerase (PDI), or that portion thereof containing the thioredoxin-like domain, and its various species' homologs [J. E. Edman et al., Nature 317:267–270 (1985)] may also be employed as a thioredoxin-like DNA sequence, since a repeated domain of PDI shares >30% homology with *E. coli* thioredoxin and that repeated domain contains an active-site loop structurally and functionally equivalent to the Cys . . . Cys active-site loop of *E. coli* thioredoxin. These three publications are incorporated herein by reference for the purpose of providing information on glutaredoxin and PDI which is known and available to one of skill in the art.

Similarly the DNA sequence encoding phosphoinositide-specific phospholipase C (PI-PLC), fragments thereof and various species' homologs thereof [C. F. Bennett et al., Nature 334:268–270 (1988)] may also be employed in the present invention as a thioredoxin-like sequence based on their amino acid sequence homology with *E. coli* thioredoxin, or alternatively based on similarity in three-dimensional confirmation and the presence of an active-site loop structurally and functionally equivalent to the Cys . . . Cys active-site loop of *E. coli* thioredoxin. All or a portion of the DNA sequence encoding an endoplasmic reticulum protein, such as ERp72, or various species homologs thereof are also included as thioredoxin-like DNA sequences for the purposes of this invention [R. A. Mazzarella et al., J. Biol. Chem. 265:109–1101 (1990)] based on amino acid sequence homology, or alternatively based on similarity in three-dimensional confirmation and the presence of an active-site loop structurally and functionally equivalent to the Cys . . . Cys active-site loop of *E. coli* thioredoxin. Another thioredoxin-like sequence is a DNA sequence which encodes all or a portion of an adult T-cell leukemia-derived factor (ADF) or other species homologs thereof [N. Wakasugi et al., Proc. Natl. Acad. Sci. USA 87:8282–8286 (1990)]. ADF is now believed to be human thioredoxin. Similarly, the protein responsible for promoting disulfide bond formation in the periplasm of *E.coli*, the product of the dsbA gene (J. C. Bardwell et al , Cell 67: 581–589 (1991), also can be considered a thioredoxin-like sequence. These four publications are incorporated herein by reference for the purpose of providing information on PI-PLC, ERp72, ADF, and dsbA which are known and available to one of skill in the art.

It is expected from the definition of thioredoxin-like DNA sequence used above that other sequences not specifically identified above, or perhaps not yet identified or published, may be thioredoxin-like sequences either based on the 30% amino acid sequence homology to *E. coli* thioredoxin or based on having three-dimensional structures substantially similar to *E. coli* or human thioredoxin and having an active-site loop functionally and structurally equivalent to the Cys . . . Cys active-site loop of *E. coli* thioredoxin. One skilled in the art can determine whether a molecule has these latter two characteristics by comparing its three-dimensional structure, as analyzed for example by x-ray crystallography or 2dimensional NMR spectroscopy, with the published three-dimensional structure for *E. coli* thioredoxin and by analyzing the amino acid sequence of the molecule to determine whether it contains an active-site loop that is structurally and functionally equivalent to the Cys. . . . Cys active-site loop of *E. coli* thioredoxin. By "substantially similar" in three-dimensional structure or confirmation is meant as similar to *E. coli* thioredoxin as is glutaredoxin. In addition a predictive algorithm has been described which enables the identification of thioredoxin-like proteins via computer-assisted analysis of primary sequence (L. B. Ellis et al, Biochemistry 31: 4882–91 (1992)). Based on the above description, one of skill in the art will be able to select and identify, or, if desired, modify, a thioredoxin-like DNA sequence for use in this invention without resort to undue experimentation. For example, simple point mutations made to portions of native thioredoxin or native thioredoxin-like sequences which do not effect the structure of the resulting molecule are alternative thioredoxin-like sequences, as are allelic variants of native thioredoxin or native thioredoxin-like sequences.

DNA sequences which hybridize to the sequence for *E. coli* thioredoxin (SEQ ID NO:21) or its structural homologs under either stringent or relaxed hybridization conditions also encode thioredoxin-like proteins for use in this invention. An example of one such stringent hybridization condition is hybridization at 4×SSC at 65° C., followed by a washing in 0.1XSSC at 65° C. for an hour. Alternatively an exemplary stringent hybridization condition is in 50% formamide, 4XSSC at 42° C. Examples of non-stringent hybridization conditions are 4×SSC at 50° C. or hybridization with 30–40% formamide at 42° C. The use of all such thioredoxin-like sequences are believed to be encompassed in this invention.

Construction of a fusion sequence of the present invention, which comprises the DNA sequence of a selected peptide or protein and the DNA sequence of a thioredoxin-like sequence, employs conventional genetic engineering techniques. See, Sambrook et al., Molecular Cloning. A Laboratory Manual., Cold Spring Harbor Laboratory, Cold Spring Harbor, N.Y. (1989). Fusion sequences may be prepared in a number of different ways. For example, the selected heterologous protein may be fused to the amino terminus of the thioredoxin-like molecule. Alternatively, the selected protein sequence may be fused to the carboxyl terminus of the thioredoxin-like molecule. Small peptide sequences could also be fused to either of the above-mentioned positions of the thioredoxin-like sequence to produce them in a structurally unconstrained manner.

This fusion of a desired heterologous peptide or protein to the thioredoxin-like protein increases the stability of the peptide or protein. At either the amino or carboxyl terminus, the desired heterologous peptide or protein is fused in such a manner that the fusion does not destabilize the native structure of either protein. Additionally, fusion to the soluble thioredoxin-like protein improves the solubility of the selected heterologous peptide or protein.

It may be preferred for a variety of reasons that peptides be fused within the active-site loop of the thioredoxin-like molecule. The region on the surface of thioredoxin surrounding the active-site loop has evolved, in keeping with the protein's major function as a non-specific protein disulfide oxido-reductase, to be able to interact with a wide variety of other protein surfaces, and so may be especially tolerant to the presence of inserted sequences. In addition the active-site loop region is bounded by segments of strong secondary structure, which provides many advantages for peptide fusions. Any small peptide inserted into the active-site loop of a thioredoxin-like protein is present in a region of the protein which is not involved in maintaining tertiary structure. Therefore the structure of such a fusion protein is stable. Indeed previous work has shown that $E.$ $coli$ thioredoxin can be cleaved into two fragments at a position close to the activesite loop, and yet the tertiary interactions stabilizing the protein remain intact.

The active-site loop of $E.$ $coli$ thioredoxin (SEQ ID NO:22) has the sequence $NH_2$ ... $Cys_{33}$-Gly-Pro-$Cys_{36}$ ... COOH. Fusing a selected peptide with a thioredoxin-like protein in the active-site loop portion of the protein constrains the peptide at both ends, reducing the degrees of conformational freedom of the peptide, and consequently reducing the number of possible alternative structures taken by the peptide. The inserted peptide is bound at each end by cysteine residues, which may form a disulfide linkage to each other as they do in native thioredoxin and further limit the conformational freedom of the inserted peptide.

Moreover, this invention places the peptide on the surface of the thioredoxin-like protein. Thus the invention provides a distinct advantage for use of the peptides in screening for bioactive peptide conformations and other assays by presenting peptides inserted in the active-site loop in this structural context.

Additionally the fusion of a peptide into the loop protects it from the actions of $E.$ $coli$ amino- and carboxyl-peptidases. Further, a restriction endonuclease cleavage site RsrII already exists in the portion of the $E.$ $coli$ thioredoxin DNA sequence (SEQ ID NO:21) encoding the loop region at precisely the correct position for a peptide gene fusion. (See FIG. 4.) RsrII recognizes the DNA sequence CGG(A/T)CCG leaving a three nucleotide long 5'-protruding sticky end. DNA bearing the complementary sticky ends will therefore insert at this site in only one orientation.

Yet another embodiment of the invention comprises modified fusion proteins having affinity for metal (metal ion) affinity matrices, whereby one or more specific metal-binding or metal-chelating amino acid residues are introduced e.g., via addition, deletion, or substitution, into the fusion protein sequence. Optimally the fusion partner, e.g., the thioredoxin-like sequence, is so modified; however the protein of interest could also be altered to provide a metal-binding site if such modifications could be achieved without adversely effecting a ligand binding site, an active site, or other functional sites, and/or destroying important tertiary structural relationships in the protein. These metal-binding or metal-chelating residues may be all the same or different, and can be selected from the group consisting of cysteine, histidine, aspartate, tyrosine, tryptophan, lysine, and glutamate, and are located so as to permit binding or chelation of the expressed fusion protein to a metal. Histidine is currently preferred. The metal-binding/chelating residues are situated with reference to the overall tertiary structure of the fusion protein, and the stereochemical arrangement is adapted preferably so as to permit binding/chelation to the metal and yet so as not to interfere with the expression of the fusion and so as not to interfere with the protein's biological activity.

The modification can be either to the fusion partner, the protein of interest, and/or both. In practice, the modification can be achieved with any protein, whether a fusion protein or not. Specifically, to modify any protein or the thioredoxin-like portion of the fusion protein, or, the protein of interest so as to have affinity for metal affinity matrices, it is desirable to create a "patch" on the surface of the molecule that contains a sufficient number of potential metal-binding/chelating amino acid residues in a proximity to each other to permit binding/chelation of the fusion protein to, e.g., a metal-chelating matrix. The general location for this "patch" is selected considering the following criteria: i) high solvent accessibility of the region to allow for easy binding of the protein to both metal ions and thence to the affinity matrix, and ii) a physical separation from those other regions of the molecule that might later be required for other purposes or for biological activity, for example the carboxyl-terminus and active-site loop of thioredoxin, which are both commonly used as the sites of fusion to other proteins and peptides.

Once a suitable location for the "patch" is selected based on these criterion, the specific residues that are to be mutated to metal-binding/chelating residues are chosen by three further criteria: i) high solvent exposure of their amino-acid side-chains, ii) their lack of involvement in stabilizing tertiary structural interactions and iii) their high potential mobility, ie., surface side chains not involved in protein tertiary interactions and which are free to adopt a variety of alternative conformations on the protein surface. Two such side chains positioned close to each other can adopt a configuration and spacing with respect to each other that will allow for a stable complex to be formed with a metal or metal ion. Typically, in such chelate complexes, the metal ion lies approximately 2 Å from each of the side chain coordinating atoms. Thus, when making the "patch", the positioning of the surface side chains should be such as to allow for this stable complex formation; in other words, the metal-binding amino acid residues are located to permit binding of the protein to the metal.

These modifications can be made in either the fusion partner (e.g., the thioredoxin portion of the fusion protein) or in the protein of interest portion of the molecule. The former is preferred since one can ensure retention of the biological activity of the protein of interest by modifying the fusion partner. Note that the location(s) of the amino-acid residues chosen for modification are not selected based on their involvement in any element of secondary structure, but rather solely on their meeting the above criteria. This greatly expands the total number of metal-chelating sites which potentially could be introduced into any particular protein.

To apply the above criteria, it is helpful to possess some knowledge of the tertiary/quaternary structure of the protein to be modified. The secondary structural elements of the protein, i.e., α-helix, and β-sheet structures, however, are not considered. Surprisingly, it has been found that contrary to the teachings of the prior art, the secondary structure is irrelevant to whether metal binding occurs. It is sufficient to generate an accessible site, e.g., a binding/chelating site, generally, on the surface of the molecule in accordance with the criteria detailed above. The histidine patch can comprise replacement of residues that happen to be in a region whose secondary structure is labeled α-helix or β-sheet, although it is not necessary according to the present invention. It suffices that the modifications undertaken result in the generation of a metal binding/chelating site in an exposed position, e.g., on the surface of the molecule. It has been found that one such "patch" is sufficient; however, depending upon the nature of the protein to be purified, it may be desirable to increase the level of binding of the protein by designing in more than one "patch."

Specifically, the amino acid residues at positions 2, 31, and 63 of *E. coli* thioredoxin, as shown in FIG. 7 (SEQ ID NOS:25 and 26), where amino acid 2 is serine, 31 is glutamate, and 63 is glutamine, were changed to histidine residues by standard methods. In an alternative embodiment, only residues 31 and 63 were changed to histidine. By changing these residues to histidines, it has been found that both thioredoxin variants bind with much greater affinity than does wild-type thioredoxin to metal-ioncharged chelating Sepharose FF (Pharmacia). In yet another embodiment, the amino acids at other positions in *E. coli* thioredoxin are similarly changed to metal binding/chelating amino acids.

A fusion sequence of a thioredoxin-like sequence with a desired protein or peptide sequence according to this invention may optionally contain a linker peptide inserted between the thioredoxin-like sequence and the selected heterologous peptide or protein. This linker sequence may encode, if desired, a polypeptide which is selectively cleavable or digestible by conventional chemical or enzymatic methods. For example, the selected cleavage site may be an enzymatic cleavage site. Examples of enzymatic cleavage sites include sites for cleavage by a proteolytic enzyme, such as enterokinase, Factor Xa, trypsin, collagenase, and thrombin. Alternatively, the cleavage site in the linker may be a site capable of being cleaved upon exposure to a selected chemical, e.g., cyanogen bromide, hydroxylamine, or low pH.

Cleavage at the selected cleavage site enables separation of the heterologous protein or peptide from the thioredoxin fusion protein to yield the mature heterologous peptide or protein. The mature peptide or protein may then be obtained in purified form, free from any polypeptide fragment of the thioredoxin-like protein to which it was previously linked. The cleavage site, if inserted into a linker useful in the fusion sequences of this invention, does not limit this invention. Any desired cleavage site, of which many are known in the art, may be used for this purpose.

The optional linker sequence of a fusion sequence of the present invention may serve a purpose other than the provision of a cleavage site. The linker may also be a simple amino acid sequence of a sufficient length to prevent any steric hindrance between the thioredoxin-like molecule and the selected heterologous peptide or protein. In addition, the linker sequence provides for post-translational modification including, but not limited to, e.g., phosphorylation sites, biotinylation sites, sulfation sites, γ-carboxylation sites, and the like.

Whether or not such a linker sequence is desirable will depend upon the structural characteristics of the selected heterologous peptide or protein and whether or not the resulting fusion protein is useful without cleavage. For example, where the thioredoxin-like sequence is a human sequence, the fusion protein may itself be useful as a therapeutic or as a vaccine without cleavage of the selected protein or peptide therefrom. Alternatively, where the mature protein sequence may be naturally cleaved, no linker may be needed.

The length and amino acid composition of the linker sequence can influence the level of production for particular fusions, e.g., production levels of the thioredoxin-IL-11 fusion of Example 1 are very sensitive to any changes in the linker sequence, both in terms of length and composition. In contrast expression levels of other fusions are insensitive to linker sequence alterations e.g., various thioredoxin-MIP-1α fusion proteins with linker sequences comprising 0–40 alternating gly-ser residues each accumulated to similar levels. Whether a particular fusion is sensitive to linker length and/or composition can be readily determined empirically without undue experimentation by one skilled in the art using standard techniques.

In one embodiment therefore, the fusion sequence of this invention contains a thioredoxin-like sequence fused directly at its amino or carboxyl terminal end to the sequence of the selected peptide or protein. The resulting fusion protein is thus a soluble cytoplasmic fusion protein. In another embodiment, the fusion sequence further comprises a linker sequence interposed between the thioredoxin-like sequence and the selected peptide or protein sequence. This fusion protein is also produced as a soluble cytoplasmic protein. Similarly, where the selected peptide sequence is inserted into the active-site loop region or elsewhere within the thioredoxin-like sequence, a cytoplasmic fusion protein is produced. The cytoplasmic fusion protein can be purified by conventional means.

Preferably, as a novel aspect of the present invention, several thioredoxin fusion proteins of this invention may be purified by exploiting an unusual property of thioredoxin. The cytoplasm of *E. coli* is effectively isolated from the external medium by a cell envelope comprising two membranes, inner and outer, separated from each other by a periplasmic space within which lies a rigid peptidoglycan cell wall. The peptidoglycan wall contributes both shape and strength to the cell. At certain locations in the cell envelope there are "gaps" (called variously Bayer patches, Bayer junctions or adhesion sites) in the peptidoglyean wall where the inner and outer membranes appear to meet and perhaps fuse together. See, M. E. Bayer, J. Bacteriol. 93:1104–1112 (1967) and J. Gen. Microbiol. 53:395–404 (1968). Most of the cellular thioredoxin lies loosely associated with the inner surface of the membrane at these adhesion sites and can be quantitatively expelled from the cell through these adhesion sites by a sudden osmotic shock or by a simple freeze/thaw procedure. See C. A. Lunn and V. P. Pigiet, J. Biol. Chem. 257:11424–11430 (1982) and in "Thioredoxin and Glutaredoxin Systems: Structure and Function, p165–176, (1986) ed. A. Holmgren et al., Raven Press, New York. To a lesser extent some EF-Tu (elongation factor-Tu) can be expelled in the same way [Jacobson et al., Biochemistry 15:2297–2302 (1976)], but, with the exception of the periplasmic contents, the vast majority of *E. coli* proteins cannot be released by these treatments.

Although there have been reports of the release by osmotic shock of a limited number of heterologous proteins produced in the cytoplasm of *E. coli* (Denefle et al., Gene 85:499–510 (1989); Joseph-Liauzun et al., Gene 86:291–295 (1990); Rosenwasser et al., J. Biol. Chem. 265:13066–13073 (1990)), the ability to be so released is a rare and desirable property not shared by the majority of heterologous proteins. Fusion of a selected, desired heterologous protein to thioredoxin as described by the present invention not only enhances its production, solubility and stability as described above, but may also provide for its release from the cell by osmotic shock or freeze/thaw treatments, greatly simplifying its purification. The thioredoxin portion of the fusion protein in some cases, e.g., with MIP-1α, directs the fusion protein towards the adhesion sites, from where it can be released to the exterior by these treatments.

In another embodiment the present invention may employ another component, that is, a secretory leader sequence, among which many are known in the art, e.g., leader sequences of phoA, MBP, β-lactamase, operatively linked in frame to the fusion protein of this invention to enable the synthesis and secretion of the mature fusion protein into the bacterial periplasmic space or culture medium. This leader sequence may be fused to the amino terminus of the thioredoxin-like molecule when the selected peptide or protein sequence is fused to the carboxyl terminus or to an internal site within the thioredoxin-like sequence. An optional linker could also be present when the peptide or protein is fused at the carboxyl terminus. It is expected that this fusion sequence construct when expressed in an appropriate host cell would be produced as a secreted fusion protein rather than a cytoplasmic fusion protein. However stability, solubility and high level synthesis should characterize fusion proteins produced using any of these alternative embodiments.

This invention is not limited to any specific type of peptide or protein. A wide variety of heterologous (i.e., foreign in reference to the host genome) genes or gene fragments are useful in forming the fusion sequences of the present invention. Any selected, desired DNA sequence could be used. While the compositions and methods of this invention are most useful for peptides or proteins which are not produced, produced in inclusion bodies, or produced in very small amounts in bacterial and yeast hosts, the heterologous, selected, desired peptides or proteins can include any peptide or protein useful for human or veterinary therapy, diagnostic or research applications in any expression system. For example, hormones, cytokines, growth or inhibitory factors, enzymes, modified or wholly synthetic proteins or peptides can be produced according to this invention in bacterial, yeast, mammalian or other eukaryotic cells and expression systems suitable therefor.

In the examples below illustrating this invention, the cDNAs expressed by this invention include those encoding IL-11, MIP-1α, IL6, M-CSF, a bone inductive factor called BMP-2, or any of the BMP family, IL-2, IL-3, IL-4, IL-5, MIF, Steel Factor, MIF (macrophage inhibitory factor) and a variety of small peptides of random sequence. These proteins include examples of proteins which, when produced without a thioredoxin fusion partner, are unstable in E. coli or are found in inclusion bodies. In addition other proteins have been successfully synthesized in biologically active forms as thioredoxin fusions, e.g., G-CSF, IL-8, the catalytic subunit of bovine enterokinase, and IL1-β.

When expressing these thioredoxin fusion genes the exact growth temperature is an important variable to consider for the production of soluble proteins. Some thioredoxin fusion proteins are produced in soluble forms only at lower production temperatures, and for any particular fusion both the optimum temperature and the optimum period for fusion protein production should be determined empirically in a few simple initial experiments. A broad range of temperatures, in the range of approximately 12° C.–37° C. should be examined, with longer production times (up to 24 h) for lower temperatures and shorter production times (3–4 h) for higher temperatures. For example, it has been found that optimal production of IL-11 occurs at 37° C.; IL-2, IL-3 and IL-4 at 15° C.; LIF, IL6 and BMP-2 at 25° C.; and M-CSF, murine SF and MIP-1α at 37° C.; the exact optima of the time and temperature is determined empirically without undue experimentation by one skilled in the art using standard techniques.

A variety of DNA molecules incorporating the above-described fusion sequences may be constructed for producing the selected peptide or protein according to this invention. At a minimum a desirable DNA sequence according to this invention comprises a fusion sequence described above, in association with, and under the control of, an expression control sequence capable of directing the expression of the fusion gene in a desired host cell. For example, where the host cell is an E. coli strain, the DNA molecule desirably contains a promoter which functions in E. coli, a ribosome binding site, and optionally, a selectable marker gene and an origin of replication if the DNA molecule is extra-chromosomal. Numerous bacterial expression vectors containing these components are known in the art for bacterial expression, and can easily be constructed by standard molecular biology techniques. Similarly, known yeast and mammalian cell vectors and vector components may be utilized where the host cell is a yeast cell or a mammalian cell.

The DNA molecules containing the fusion sequences may be further modified to contain different codons to optimize expression in the selected host cell, as is known in the art. These DNA molecules may additionally contain multiple copies of the thioredoxin-like DNA sequence, with the heterologous protein gene fused to only one of the DNA sequences, or with the heterologous protein gene fused to all copies of the thioredoxin-like sequence. It may also be possible to integrate a thioredoxin-like/heterologous peptide or protein-encoding fusion sequence into the chromosome of a selected host to either replace or duplicate a native thioredoxin-like sequence.

Host cells suitable for the present invention are preferably bacterial cells. For example, the various strains of E. coli (e.g., HB101, W3110 and strains used in the following examples) are well-known as host cells in the field of biotechnology. E. coli strain GI724, used in the following examples, has been deposited with a United States microorganism depository as described in detail below. Various strains of B. subtilis, Pseudomonas, and other bacteria may also be employed in this method.

Many strains of yeast and other eukaryotic cells known to those skilled in the art may also be useful as host cells for expression of the polypeptides of the present invention. For example, Saccharomyces cerevisiae strain EGY-40 has been used by these inventors as a host cell in the production of various small peptide/thioredoxin fusions. It could be preferably used instead of E. coli as a host cell in the production of any of the proteins exemplified herein. Similarly known mammalian cells may also be employed in the synthesis of these fusion proteins.

To produce the fusion protein of this invention, the host cell is either transformed with, or has integrated into its genome, a DNA molecule comprising a thioredoxin-like DNA sequence fused to the DNA sequence of a selected heterologous peptide or protein, desirably under the control of an expression control sequence capable of directing the expression of a fusion protein. The host cell is then cultured under known conditions suitable for fusion protein production. If the fusion protein accumulates in the cytoplasm of the cell it may be released by conventional bacterial cell lysis techniques and purified by conventional procedures including selective precipitations, solubilizations and column chromatographic methods, and also including metal-chelate affinity columns where metal-binding amino acid residues are present in the protein or fusion protein or in the thioredoxin-like region where a thioredoxin variant is used as the fusion partner. If a secretory leader is incorporated into the fusion molecule substantial purification is achieved when the fusion protein is secreted into the periplasmic space or the growth medium.

Alternatively, for cytoplasmic thioredoxin fusion proteins, a selective release from the cell may be achieved by osmotic shock or freeze/thaw procedures. Although final purification is still required for most purposes, the initial purity of fusion proteins in preparations resulting from these procedures is superior to that obtained in conventional whole cell lysates, reducing the number of subsequent purification steps required to attain homogeneity. In a typical osmotic shock procedure, the packed cells containing the fusion protein are resuspended on ice in a buffer containing EDTA and having a high osmolarity, usually due to the inclusion of a solute, such as 20% w/v sucrose, in the buffer which cannot readily cross the cytoplasmic membrane. During a brief incubation on ice the cells plasmolyze as water leaves the cytoplasm as a result of the osmotic gradient. The cells are then switched into a buffer of low osmolarity, and during the osmotic re-equilibration both the contents of the periplasm and proteins localized at the Bayer patches are released to the exterior. A simple centrifugation following this release removes the majority of bacterial cell-derived contaminants from the fusion protein preparation. Alternatively, in a freeze/thaw procedure the packed cells containing the fusion protein are first resuspended in a buffer containing EDTA and are then frozen. Fusion protein release is subsequently achieved by allowing the frozen cell suspension to thaw. The majority of contaminants can be removed as described above by a centrifugation step. The fusion protein is further purified by well-known conventional methods.

These treatments frequently release a substantial proportion of the fusion proteins without lysing the cell cultures. The success of these procedures in releasing significant amounts of several thioredoxin fusion proteins is surprising, since such techniques are not generally successful with a wide range of proteins. The ability of these fusion proteins to be substantially purified by such treatments, which are significantly simpler and less expensive than the purification methods required by other fusion protein systems, may provide the fusion proteins of the invention with a significant advantage over other systems which are used to produce proteins in E. coli.

In yet another purification method, it is possible to readily purify the protein or protein fusions comprising modified forms of the protein, or fusion protein, or thioredoxin-like molecules, having one or more metal-binding/chelating amino acids introduced into the sequence of the thioredoxin-like sequence, by utilizing the affinity of the modified protein for binding and/or chelation to an immobilized metal ion, such as $Cu^{2+}$, $Ni^{2+}$, $Co^{2+}$, $Zn^{2+}$, $Fe^{2+}$, $Cd^{2+}$, $Ca^{2+}$ and the like. The actual ion(s) chosen depends upon the nature of the protein to be purified, the nature of the environment from which the protein is to be purified, the degree of binding desired, and the tolerance of the protein for the correspondingly appropriate elution buffer, as is readily apparent to one skilled in the art.

Useful metal (metal ion) affinity matrices/resins include any matrix or resin for which metals (metal ions) have affinity. These include, for example, fast flow chelating Sepharose (Pharmacia) which uses an immobilized imino-diacetic acid (IDA) group to bind the metal ion, or NTA agarose (Quiagen) which uses a nitrilo-tri-acetic acid group, or Poros MC (Perceptive Biosystems), or Fractogel EMD Chelate GSO (EM Separations). Appropriately useful solvent systems for initial binding or chelation are readily selected by one skilled in the art. For example, the chelating of the metal-chelating thioredoxin fusions to the aforementioned columns can be achieved in suitable buffers such as tris, phosphate, or acetate in the pH range of 6–8. The inclusion of high salt concentrations in the binding buffer (e.g., 0.5M NaCl) will abolish most non-specific ionic interactions with the column matrix, but without preventing the desired chelate formation. Thus, a higher percentage of the protein of interest can be bound, with the remaining contaminants and impurities simply flowing through. Any elution buffer which competes with the metal binding residues on the protein (e.g., histidine residues) or with the metal binding groups on the column will be effective as is readily apparent to one skilled in the art and includes, but is not limited to, such buffers containing, e.g., imidazole, or chelators such as EDTA, EGTA, and the like. Also useful elution buffers are those in which the pH is such that the metal binding residues on the protein can no longer effectively chelate metal ions.

The resulting fusion protein is stable and soluble, often with the heterologous peptide or protein retaining its bioactivity. The heterologous peptide or protein may,optionally be separated from the thioredoxin-like protein by cleavage, as discussed above. In an alternative embodiment, it is possible to subject the fusion protein to cleavage just after binding to the metal affinity matrix but before elution.

In the specific and illustrative embodiments of the compositions and methods of this invention, the E. coli thioredoxin (trxA) gene (SEQ ID NO:21) has been cloned and placed in an E. coli expression system. An expression plasmid pALtrxA-781 was constructed. A related plasmid containing modified IL-11 fused to the thioredoxin sequence and called pALtrxA/EK/IL11ΔPro-581 (SEQ ID NO:13 and SEQ ID NO:14) is described below in Example 1 and in FIG. 1. The expression of a thioredoxin-IL-11 fusion protein using this plasmid in a suitable E. coli host strain, the purification of this fusion protein by conventional lysis and chromatographic techniques, subsequent enzymatic cleavage of the fusion by bovine enterokinase and the chromatographic separation of the cleaved IL-11 from its thioredoxin fusion partner is described in Example 2 below. Therein are also described properties of the purified IL-11 protein. A modified version of pALtrxA/EK/IL11ΔPro-581 containing a different ribosome binding site and lacking the sequences for IL-11 is employed in the other examples and is specifically described in Example 3. Other conventional vectors may be employed in this invention. The invention is not limited to the plasmids described in these examples.

Plasmid pALtrxA-781 (without the modified IL-11) directs the accumulation of >10% of the total cell protein as thioredoxin in E. coli host strain GI724. Examples 3 through 11 describe the use of this plasmid to form and express thioredoxin fusion proteins with MIP-1α (SEQ ID NO:16), BMP-2 (SEQ ID NO:18), IL-2, IL-3, IL-4, IL-5, LIF, Steel Factor, and MIF. Example 13 describes a fusion of thioredoxin to IL-6 (SEQ ID NO:20) and Example 14 a thioredoxin fusion to M-CSF (SEQ ID NO:24).

As an example of the expression of small peptide genes inserted into the active-site loop, a derivative of pALtrxA-781 has been constructed in which a 13 amino-acid linker peptide sequence containing a cleavage site for the specific protease enterokinase (Leipnieks and Light, J. Biol. Chem. 254:1077–1083 (1979)) has been fused into the active-site loop of thioredoxin. This plasmid (pALtrxA-EK) directs the accumulation of >10% of the total cell protein as the fusion protein. The fusion protein is fully soluble, indicating that it has probably adopted a 'native' tertiary structure. It is equally as stable as wild type thioredoxin to prolonged incubations at 80° C., suggesting that the strong tertiary structure of thioredoxin has not been compromised by the insertion into the active-site loop. The fusion protein is specifically cleaved by enterokinase, whereas thioredoxin is not, indicating that the peptide inserted into the active-site loop is accessible to a large, bulky protease and is probably present on the surface of the fusion protein.

As described in more detail in Example 12 below, fusions of small peptides (SEQ ID NO:1 through SEQ ID NO:12) were made into the active-site loop of thioredoxin. The inserted peptides were 14 residues long and were of totally random composition to test the ability of the system to deal with hydrophobic, hydrophilic and neutral sequences.

The methods and compositions of this invention permit the production of proteins and peptides useful in research, diagnostic and therapeutic fields. The production of fusion proteins according to this invention has a number of advantages. As one example, the production of a selected protein by the present invention as a carboxyl-terminal fusion to $E.$ $coli$ thioredoxin (SEQ ID NO:21), or another thioredoxin-like protein, enables avoidance of translation initiation problems often encountered in the production of eukaryotic proteins in $E.$ $coli$. Additionally the initiator methionine usually remaining on the amino-terminus of the heterologous protein is not present and therefore does not have to be removed when the heterologous protein is made as a carboxyl terminal thioredoxin fusion.

The production of fusion proteins according to this invention reliably improves solubility of desired heterologous proteins and enhances their stability to proteases in the host cell. This invention also enables high level synthesis of certain desirable therapeutic proteins, e.g., IL-11, which are otherwise produced at low levels in bacterial hosts.

This invention may also confer heat stability to the fusion protein, especially if the heterologous protein itself is heat stable. Because thioredoxin, and presumably all thioredoxin-like proteins are heat stable up to 80° C., the present invention may enable the use of a simple heat treatment as an initial effective purification step for some thioredoxin fusion proteins. An example of such a simple heat-treatment purification procedure is provided by Example 3.

In addition to providing high levels of the selected heterologous proteins or peptides upon cleavage from the fusion protein for therapeutic or other uses, the fision proteins or fusion peptides of the present invention may themselves be useful as therapeutics provided the thioredoxin-like protein is not antigenic to the animal being treated. Further the thioredoxin-like fusion proteins may provide a vehicle for the delivery of bioactive peptides. As one example, human thioredoxin would not be antigenic in humans, and therefore a fusion protein of the present invention with human thioredoxin may be useful as a vehicle for delivering to humans the biologically active peptide to which it is fused. Because human thioredoxin is an intracellular protein, human thioredoxin fusion proteins may be produced in an $E.$ $coli$ intracellular expression system. Thus this invention also provides a method for delivering biologically active peptides or proteins to a patient in the form of a fusion protein with an acceptable thioredoxin-like protein.

The present invention also provides methods and reagents for screening libraries of random peptides for their potential enzyme inhibitory, hormone/growth factor agonist and hormone/growth factor antagonist activity. Also provided are methods and reagents for the mapping of known protein sequences for regions of potential interest, including receptor binding sites, substrate binding sites, phosphorylation/modification sites, protease cleavage sites, and epitopes.

Bacterial colonies expressing thioredoxin-like/random peptide fusion genes may be screened using radiolabelled proteins such as hormones or growth factors as probes. Positives arising from this type of screen identify mimics of receptor binding sites and may lead to the design of compounds with therapeutic uses. Bacterial colonies expressing thioredoxin-like random peptide fusion genes may also be screened using antibodies raised against native, active hormones or growth factors. Positives arising from this type of screen could be mimics of surface epitopes present on the original antigen. Where such surface epitopes are responsible for receptor binding, the 'positive' fusion proteins have biological activity.

Additionally, the thioredoxin-like fusion proteins or fusion peptides of this invention may also be employed to develop monoclonal and polyclonal antibodies, or recombinant antibodies or chirneric antibodies, generated by known methods for diagnostic, purification or therapeutic use. Studies of thioredoxin-like molecules indicate a possible B cell/T cell growth factor activity [N. Wakasuki et al., cited above], which may enhance immune response. The fusion proteins or peptides of the present invention may be employed as antigens to elicit desirable antibodies, which themselves may be further manipulated by known techniques to yield monoclonal or recombinant antibodies.

Alternatively, antibodies elicited to thioredoxin-like sequences may also be useful in the purification of many different thioredoxin fusion proteins. The following examples illustrate embodiments of the present invention, but are not intended to limit the scope of the disclosure.

EXAMPLE 1

Thioredoxin/IL-11 Fusion Molecule

A thioredoxin-like fusion molecule of the present invention was prepared using $E.$ $coli$ thioredoxin as the thioredoxin-like sequence and recombinant IL-11 [Paul et al, Proc. Natl. Acad. Sci. U.S.A. 87:7512–7516 (1990); see also, copending U.S. patent applications Ser. No. 07/526, 474, and Ser. No. 07/441,100 and PCT Patent publication WO91/07495, published May 30, 1991 incorporated herein by reference] as the selected heterologous protein. The $E.$ $coli$ thioredoxin (trxA) gene (SEQ ID NO:21) was cloned based on its published sequence and employed to construct various related $E.$ $coli$ expression plasmids using standard DNA manipulation techniques, described extensively by Sambrook, Fritsch and Maniatis, Molecular Cloning. A Laboratory Manual, 2nd edition, Cold Spring Harbor Laboratory, Cold Spring Harbor, N.Y. (1989).

A first expression plasmid pALtrxA-781 was constructed containing the E. coli trxA gene without fusion to another sequence. This plasmid further contained sequences which are described in detail below for the related IL-11 fusion plasmid. This first plasmid, which directs the accumulation of >10% of the total cell protein as thioredoxin in an E. coli host strain GI724, was further manipulated as described below for the construction of a trxA/IL-11 fusion sequence.

Alternatively, a thioredoxin-like molecule modified to include metal-binding/chelating amino acid residues, such as, eg., histidine residues at positions 2, 31 and 63, or, alternatively, at positions 31 and 63, was prepared as described in greater detail in Example 18, using standard DNA manipulation techniques (reference above).

The entire sequence of the related plasmid expression vector, pALtrx/EK/IL11ΔPro-581 (SEQ ID NO:13 and SEQ ID NO:14), is illustrated in FIG. 1 and contains the following principal features:

Nucleotides 1–2060 contain DNA sequences originating from the plasmid pUC-18 [Norrander et al, Gene 26: 101–106 (1983)] including sequences containing the gene for β-lactamase which confers resistance to the antibiotic ampicillin in host E. coli strains, and a colE1-derived origin of replication. Nucleotides 2061–2221 contain DNA sequences for the major leftward promoter (pL) of bacteriophage λ [Sanger et al., J. Mol. Biol. 162:729–773 (1982)], including three operator sequences, $O_L1$, $O_L2$ and $O_L3$. The operators are the binding sites for λcI repressor protein, intracellular levels of which control the amount of transcription initiation from pL. Nucleotides 2222–2241 contain a strong ribosome binding sequence derived from that of gene 10 of bacteriophage T7 [Dunn and Studier, J. Mol. Biol. 166:477–535 (1983)].

Nucleotides 2242–2568 contain a DNA sequence encoding the E. coli thioredoxin protein (SEQ ID NO:21) [Lim et al., J. Bacteriol. 163:311–316 (1985)]. There is no translation termination codon at the end of the thioredoxin coding sequence in this plasmid.

Nucleotides 2569–2583 contain DNA sequence encoding the amino acid sequence for a short, hydrophilic, flexible spacer peptide "-GSGSG-". Nucleotides 2584–2598 provide DNA sequence encoding the amino acid sequence for the cleavage recognition site of enterokinase (EC 3.4.4.8), "-DDDDK-" [Maroux et al., J. Biol. Chem. 246:5031–5039 (1971)].

As an alternative embodiment a single additional codon can be inserted into the linker sequence of the plasmid to introduce a specific site for chemical cleavage of the thioredoxin-IL-11 fusion protein by hydroxylamine. The nucleotide triplet introduced between residues 2598 and 2599 of pALtrxA EK/IL11ΔPro-581, "-AAT-", encodes an asparagine residue. This asparagine, in combination with the glycine residue immediately following, comprises a new hydroxylamine cleavage site. Under appropriate conditions, detailed in Example 2, hydroxylamine cleavage will occur between the asparagine and glycine residues. As an additional feature of this alternative embodiment two naturally occurring asparagine residues present in wild-type thioredoxin, amino-acids 84 and 107, may be altered to glutamine by standard techniques to remove two other unwanted hydroxylamine cleavage sites, thus reducing secondary hydroxylamine cleavage products which could hamper subsequent purification procedures.

Nucleotides 2599–3132 contain DNA sequence encoding the amino acid sequence of a modified form of mature human IL-11 [Paul et al., Proc. Natl. Acad. Sci. USA 87:7512–7516 (1990)], deleted for the N-terminal prolyl-residue normally found in the natural protein. The sequence includes a translation termination codon at the 3'-end of the IL-11 sequence.

Nucleotides 3133–3159 provide a "Linker" DNA sequence containing restriction endonuclease sites. Nucleotides 3160–3232 provide a transcription termination sequence based on that of the E. coli aspA gene [Takagi et al., Nucl. Acids Res. 13:2063–2074 (1985)]. Nucleotides 3233–3632 are DNA sequences derived from pUC-18.

As described in Example 2 below, when cultured under the appropriate conditions in a suitable E. coli host strain, this plasmid vector can direct the production of high levels (approximately 10% of the total cellular protein) of a thioredoxin/IL-11 fusion protein. By contrast, when not fused to thioredoxin, IL-11 accumulated to only 0.2% of the total cellular protein when expressed in an analogous host/vector system.

EXAMPLE 2

Expression of a Fusion Protien

A thioredoxin/IL-11 fusion protein was produced according to the following protocol using the plasmid constructed as described in Example 1. pALtrxA/EK/IL11ΔPro-581 (SEQ ID NO:13) was transformed into the E. coli host strain GI724 (F⁻, $lac^q$, $lac^{L8}$, ampC::γcI⁺) by the procedure of Dagert and Ehrlich, Gene 6:23 (1979). The untransformed host strain E. coli GI724 was deposited with the American Type Culture Collection, 12301 Parklawn Drive, Rockville, Md. on Jan. 31, 1991 under ATCC No. 55151 for patent purposes pursuant to applicable laws and regulations. Transformants were selected on 1.5% w/v agar plates containing IMC medium, which is composed of M9 medium [Miller, "Experiments in Molecular Genetics", Cold Spring Harbor Laboratory, New York (1972)] containing 1 mM $MgSO_4$ and supplemented with 0.5% w/v glucose, 0.2% w/v casamino acids and 100 μg/ml ampicillin.

GI724 contains a copy of the wild-type λcI repressor gene stably integrated into the chromosome at the ampC locus, where it has been placed under the transcriptional control of Salmonella typhimurium trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the tip promoter and turn off synthesis of λcI, gradually causing the induction of transcription from pL promoters if they are present in the cell.

GI724 transformed with pALtrxA/EK/IL-11ΔPro-581 (SEQ ID NO:13 and SEQ ID NO:14) was grown at 30° C. to an $A_{550}$ of 0.5 in IMC medium. Tryptophan was added to a final concentration of 100 μg/ml and the culture incubated for a further 4 hours at 37° C. During this time thioredoxin/IL-11 fusion protein accumulated to approximately 10% of the total cell protein.

All of the fusion protein was found to be in the soluble cellular fraction, and was purified as follows. Cells were lysed in a french pressure cell at 20,000 psi in 50 mM HEPES pH 8.0, 1 mM phenylmethylsulfonyl fluoride. The lysate was clarified by centrifugation at 15,000×g for 30 minutes and the supernatant loaded onto a QAE-Toyopearl column. The flow-through fractions were discarded and the fusion protein eluted with 50 mM HEPES pH 8.0, 100 mM NaCl. The eluate was adjusted to 2M NaCl and loaded onto a column of phenyl-Toyopearl. The flow-through fractions were again discarded and the fusion protein eluted with 50 mM HEPES pH 8.0, 0.5M NaCl.

The fusion protein was then dialyzed against 25 mM HEPES pH 8.0 and was >80% pure at this stage. By T1165 bioassay [Paul et al., cited above] the purified thioredoxin/IL-11 protein exhibited an activity of $8\times10^5$U/mg. This value agrees closely on a molar basis with the activity of $2\times10^6$U/mg found for COS cell-derived IL-11 in the same assay. One milligram of the fusion protein was cleaved at 37° C. for 20 hours with 1000 units of bovine enterokinase [Leipnieks and Light, J. Biol. Chem. 254:1677–1683 (1979)] in 1 ml 10 mM Tris-Cl (pH 8.0)/10 mM $CaCl_2$. IL-11 could be recovered from the reaction products by passing them over a QAE-Toyopearl column in 25 mM HEPES pH 8.0, where IL-11 was found in the flow-through fractions. Uncleaved fusion protein, thioredoxin and enterokinase remained bound on the column.

The IL-11 prepared in this manner had a bioactivity in the T1165 assay of $2.5\times10^6$U/mg.

Its physical and chemical properties were determined as follows:

(1) Molecular Weight

The molecular weight of the IL-11 was found to be about 21 kD as measured by 10% SDS-PAGE under reducing conditions (tricine system) in accordance with the methods of Schagger, et al, *Anal Biochem*, 166:368–379 (1987). The protein ran as a single band.

(2) Endotoxin Content

The endotoxin content of the IL-11 was found to be less than 0.1 nanogram per milligram IL-11 in the LAL (Limulus amebocyte lysate, Pyrotel, available from Associates of Cape Cod, Inc., Woods Hole, Mass. U.S.A.) assay, conducted in accordance with the manufacturer's instructions.

(3) Isoelectric Point

The theoretical isoelectric point of IL-11 is pH 11.70. As measured by polyacrylamide gel isoelectric focusing using an LKB Ampholine PAGplate with a pH range from 3.5 to 9.5, the IL-11 ran at greater than 9.5. An exact measurement could not be taken because IL-11 is too basic a protein for accurate pI determinations.

(4) Fluorescence Absorption Spectrum

The fluorescence absorption spectrum of the IL-11, as measured on a 0.1% aqueous solution in a 1 cm quartz cell showed an emission maximum at 335–337 nm.

(5) UV Absorption

UV absorption of the IL-11 on a 0.1% aqueous solution in a 1 cm quartz cell showed an absorbance maximum at 278–280 nm.

(6) Amino Acid Composition

The theoretical amino acid composition for IL-11, based on its amino acid sequence is as follows:

| Amino Acid | Number | Mole % |
| --- | --- | --- |
| Ala | 20 | 11.3 |
| Asp Acid | 11 | 6.22 |
| Cysteine | 0 | |
| Glu | 3 | 1.70 |
| Phe | 1 | 0.57 |
| Gly | 14 | 7.91 |
| His | 4 | 2.26 |
| Ile | 2 | 1.13 |
| Lys | 3 | 1.70 |
| Leu | 41 | 23.16 |
| Met | 2 | 1.13 |
| Asn | 1 | 0.57 |

-continued

| Amino Acid | Number | Mole % |
| --- | --- | --- |
| Pro | 21 | 11.86 |
| Gln | 7 | 3.96 |
| Arg | 18 | 10.17 |
| Ser | 11 | 6.22 |
| Thr | 9 | 5.09 |
| Val | 5 | 2.83 |
| Trp | 3 | 1.70 |
| Tyr | 1 | 0.57 |

A sample of homogenous IL-11 was subjected to vapor phase hydrolysis as follows:

6N HCl and 2N phenol reagent were added to an hydrolysis vessel in which tubes containing 45 $\mu$l of 1:10 diluted (w/$H_2O$) IL-11, concentrated to dryness are inserted. Samples were sealed under vacuum and hydrolyzed for 36 hours at 110° C. After the hydrolysis, samples were dried and resuspended in 500 $\mu$l Na-S sample dilution buffer. Amino acid analysis was performed on a Beckman 7300 automated amino acid analyzer. A cation exchange column was used for separation of amino acids following post-column derivatization with ninhydrin. Primary amino acids were detected at 570 nm and secondary amino acids were detected at 440 nm. Eight point calibration curves were constructed for each of the amino acids.

Because certain amino acids are typically not recovered, results for only 5 amino acids are given below. Since the hydrolysis was done without desalting the protein, 100% recovery was achieved for most of the amino acids.

The relative recovery of each individual amino acid residue per molecule of recombinant IL-11 was determined by normalizing GLX=10 (the predicted number of glutamine and glutamic acid residue in IL-11 based on cDNA sequence). The value obtained for the recovery of GLX in picomoles was divided by 10 to obtain the GLX quotient. Dividing the value obtained for the recovery in picomoles of each amino acid by the GLX quotient for that sample gives a number that represents the relative recovery of each amino acid in the sample, normalized to the quantitative recovery of GLX residues. The correlation coefficient comparing the expected versus the average number of residues of each amino acid observed is greater than 0.985, indicating that the number of residues observed for each amino acid is in good agreement with that predicted sequence.

| Amino Acids | No. of Residues Calculated | No. of Residues Expected | Correlation Coefficient |
| --- | --- | --- | --- |
| 1 Asp | 12.78 | 12 | |
| 2 Glu | 10.00 | 10 | |
| 3 Gly | 12.80 | 14 | 0.9852 |
| 4 Arg | 16.10 | 18 | |
| 5 Pro | 18.40 | 21 | |

(7) Amino Terminus Sequencing

IL-11 (buffered in 95% acetonitrile TFA) was sequenced using an ABI 471A protein sequencer (ABI, Inc.) in accordance with the manufacturer's instructions. Amino terminus sequencing confirmed that the thioredoxin fusion protein produced IL-11 contained the correct IL-11 amino-acid sequence, and only one amino terminus was observed.

(8) Peptide Mapping

The IL-11 was cleaved with Endoproteinase Asp-N (Boehringer Mannheim) (1:500 ratio of Asp-N to IL-11) in 10 mM Tris, pH 8, 1M urea and 2 mM 4-aminobenzamidine dihydrochloride (PABA), at 37° C. for 4 hours. The sample was then run on HPLC on a C4 Vydac column using an A buffer of 50 mM NaHPO$_4$, pH 4.3, in dH2O, a B buffer of 100% isopropanol with a gradient at 1 ml/min from 100% A to 25% A and 75% B (changing at 1%/minute). The eluted peptide fragments were then sequenced using an ABI 471A protein sequencer (ABI, Inc.) in accordance with the manufacturer's instructions. The peptide map confirmed that the IL-11 produced from the thioredoxin fusion protein contained the expected IL-11 N-terminal and C-terminal sequences.

(9) Solubility

IL-11 protein was tested for solubility in the substances below with the following results:

| | |
|---|---|
| Water | very soluble |
| Ethyl Alcohol | very soluble |
| Acetone | very soluble |
| 1M sodium chloride | very soluble |
| 10% sucrose | very soluble |

(10) Sugar Composition and Protein/Polysaccharide Content in %

The absence of sugar moieties attached to the polypeptide backbone of the IL-11 protein is indicated by its amino acid sequence, which contains none of the typical sugar attachment sites.

When the fusion construct is made having a hydroxylamine cleavage site, cleavage is carried out as follows. A thioredoxin/IL-11 fusion protein, modified as described above to contain a hydroxylamine cleavage site between the thioredoxin and IL-11 sequences, is chemically cleaved in a reaction with hydroxylamine. The modified fusion protein at a concentration of 2.5 mg/ml is cleaved in a reaction with 1M hydroxylamine in 0.1M CHES buffer at pH 9.7. The reaction is allowed to proceed for 11 h at 35° C., and is terminated by cooling to 4° C. and lowering the pH to pH 8.0 by the addition of Tris-HCl (pH 7.3).

EXAMPLE 3

Thioredoxin/MIP-1α Fusion Molecule

Human macrophage inflammatory protein 1α (MIP-1α) (SEQ ID NO:16) can be expressed at high levels in *E. coli* as a thioredoxin fusion protein using an expression vector similar to pALtrxA/EK/IL-11ΔPro-581 described in Example 1 above but modified in the following manner to replace the ribosome binding site of bacteriophage T7 with that of λCII. In the plasrmid of Example 1, DNA sequences between nucleotides 2222 and 2241 were removed by conventional means. Inserted in place of those nucleotides was a sequence of nucleotides formed by nucleotides 35566 to 35472 and 38137 to 38361 from bacteriophage lambda as described in Sanger et al. (1982) cited above. This reference is incorporated by reference for the purpose of disclosing this sequence. To express a thioredoxin/MIP-1α fusion the DNA sequence in the thusly-modified pALtrxA/EK/IL-11ΔPro-581 encoding human IL-11 (nucleotides 2599–3132) is replaced by the 213 nucleotide DNA sequence (SEQ ID NO:15) shown in FIG. 2 encoding fill-length, mature human MIP-1α [Nakao et al., Mol. Cell. Biol. 10:3646–3658 (1990)]. In this construction the 10 amino-acid residue linker sequence, "-GSGSGDDDDK^A-" lying between thioredoxin and MIP-1α contains an enteropeptidase cleavage site (cleavage with enterokinase would occur between the lysine and alanine residues, the alanine residue is the first residue of MIP-1α). As an alternative embodiment the linker sequence between thioredoxin and MIP-1α can be omitted altogether without deleterious affects on the expression level of this fusion protein. As yet another embodiment the linker sequence may be modified to include an hydroxylamine chemical cleavage site by the insertion of an additional asparagine residue, and the alteration of the first amino-acid residue of MIP-1α from its natural alanine residue to a glycine residue. The sequence of this linker is thus "-GSGSGDDDDKN^G-", and hydroxylamine cleavage would occur between the asparagine and glycine residues.

The host strain and expression protocol used for the production of thioredoxin MIP-1α fusion protein are as described in Example 2. As was seen with the thioredoxin/IL-11 fusion protein, all of the thioredoxin/MIP-1α fusion protein was found in the soluble cellular fraction, representing up to 20% of the total protein. With the thioredoxin/MIP-1α fusion a simple heat treatment was used as an initial purification step. Cells were lysed as in Example 2 to give a protein concentration in the crude lysate of 10 mg/ml. This lysate was then heated at 80° C. for 10 min to precipitate the majority of contaminating *E. coli* proteins and was clarified by centrifugation at 130,000×g for 60 minutes. The pellet was discarded and the supernatant loaded onto a Mono Q column. The fusion protein eluted at approximately 0.5M NaCl from this column and was >80% pure at this stage. After dialysis to remove salt the fusion protein could be cleaved by an enterokinase treatment as described in Example 2 to release MIP-1α.

EXAMPLE 4

Thioredoxin/BMP-2 Fusion Molecule

Human Bone Morphogenetic Protein 2 (13MP-2) can be expressed at high levels in *E. coli* as a thioredoxin fusion protein using the modified expression vector described in Example 3. The DNA sequence encoding human IL-11 in the modified pALtrxA/EK/IL-11ΔPro-581 (nucleotides 2599–3132) is replaced by the 345 nucleotide DNA sequence (SEQ ID NO:17) shown in FIG. 3 encoding full-length, mature human BMP-2 [Wozney et al., Science 242:1528–1534 (1988)].

In this case the thioredoxin/BMP-2 fusion protein appeared in the insoluble cellular fraction when strain GI724 containing the expression vector was grown in medium containing tryptophan at 37° C. However, when the temperature of the growth medium was lowered to 20° C. the fusion protein was found in the soluble cellular fraction.

EXAMPLE 5

Thioredoxin/IL-2 Fusion Molecule

Murine interleukin 2 (IL-2) is produced at high levels in a soluble form in *E. coli* as a thioredoxin fusion protein using the modified expression vector described in Example 3. The DNA sequence encoding human IL-11 in the modified pALtrA/EK/IL-11ΔPro-581 vector (nucleotides 2599–3132) is replaced by the DNA sequence encoding murine IL-2, Genbank Accession No. K02292, nucleotides 109 to 555. The thioredoxin/IL-2 fusion gene is expressed under the conditions described for thioredoxin/IL-11 in Example 2. The culture growth temperature used in this case is 15° C. Under these conditions the majority of the thioredoxin/IL-2 fusion protein accumulates in the soluble cellular fraction.

The fusion protein can be cleaved using the enterokinase treatment described in Example 2.

EXAMPLE 6

Thioredoxin/IL-3 Fusion Molecule

Human interleuldn 3 (IL-3) is produced at high levels in a soluble form in *E. coli* as a thioredoxin fusion protein using the modified expression vector described in Example 3. The DNA sequence encoding human IL-11 in the modified pALtrA/EK/IL-11ΔPro-581 vector (nucleotides 2599–3132 is replaced by the DNA sequence encoding human IL-3, Genbank Accession No. M14743, nucleotides 67 to 465. The thioredoxin/IL-3 fusion gene is expressed under the conditions described for thioredoxin/IL-11 in Example 2. The culture growth temperature used in this case is 15° C. Under these conditions the majority of the thioredoxin 3 fusion protein accumulates in the soluble cellular fraction. The fusion protein can be cleaved using the enterokinase treatment described in Example 2.

EXAMPLE 7

Thioredoxin/IL-4 Fusion Molecule

Murine interleukin 4 (IL-4) is produced at high levels in a soluble form in *E. coli* as a thioredoxin fusion using the modified expression vector described in Example 3. The DNA sequence encoding human IL-11 in the modified pALtrxA/EK/IL-11ΔPro-581 vector (nucleotides 2599–3122 is replaced by the DNA sequence encoding murine IL-4, Genbank Accession No. M13238, nucleotides 122 to 477. The thioredoxin/IL-4 fusion gene is expressed under the conditions described for thioredoxin/IL-11 in Example 2. The culture growth temperature used in this case is 15° C. Under these conditions the majority of the thioredoxin/IL-4 fusion protein accumulates in the soluble cellular fraction. The fusion protein can be cleaved using the enterokinase treatment described in Example 2.

EXAMPLE 8

Thioredoxin/IL-5 Fusion Molecule

Murine interleukin 5 (IL-5) is produced at high levels in a soluble form in *E. coil* as a thioredoxin fusion protein using the modified expression vector described in Example 3. The DNA sequence encoding human IL-11 in the modified pALtrxA/EK/IL-11ΔPro-581 vector (nucleotides 2599–3132 is replaced by the DNA sequence encoding murine IL-5, Genbank Accession No. X04601, nucleotides 107 to 443. The thioredoxin/murine IL-5 fusion gene is expressed under the conditions described for thioredoxin/IL-11 in Example 2. The culture growth temperature used in this case is 15° C. Under these conditions the majority of the thioredoxin/murine IL-5 fusion protein accumulates in the soluble cellular fraction. The fusion protein can be cleaved using the enterokinase treatment described in Example 2.

EXAMPLE 9

Thioredoxin/LIF Fusion Molecule

Murine LIF is produced at high levels in a soluble form in *E. coli* as a thioredoxin fusion protein using the modified expression vector described in Example 3. The DNA sequence encoding human IL-11 in the modified pALtrxA/ EK/IL-11ΔPro-581 vector (nucleotides 2599–3132 is replaced by the DNA sequence encoding murine LIF, Genbank Accession No. X12810, nucleotides 123 to 734. The thioredoxin/LIF fusion gene is expressed under the conditions described for thioredoxin/IL-11 in Example 2. The culture growth temperature used in this case is 25° C. Under these conditions the majority of the thioredoxin/LIF fusion protein accumulates in the soluble cellular fraction. The fusion protein can be cleaved using the enterokinase treatment described in Example 2.

EXAMPLE 10

Thioredoxin/Steel Factor Fusion Molecule

Murine Steel Factor is produced at high levels in a soluble form in *E. coli* as a thioredoxin fusion protein using the modified expression vector described in Example 3. The DNA sequence encoding human IL-11 in the modified pALtrxA/EK/IL-11ΔPro-581 vector (nucleotides 2599–3132 is replaced by the DNA sequence encoding murine Steel Factor, Genbank Accession No. M59915, nucleotides 91 to 583. The thioredoxin/Steel Factor fusion gene is expressed under the conditions described for thioredoxin/IL-11 in Example 2. The culture growth temperature used in this case is 37° C. Under these conditions the majority of the thioredoxin/Steel Factor fusion protein accumulates in the soluble cellular fraction. The fusion protein can be cleaved using the enterokinase treatment described in Example 2.

EXAMPLE 11

Thioredoxin/MIF Fusion Molecule

Human Macrophage Inhibitory Factor (MIF) is produced at high levels in a soluble form *E. coli* as a thioredoxin fusion protein using the modified expression vector described in Example 3. The DNA sequence encodinghuman IL-11 in the modified pALtrxA/EK/IL-11ΔPro-581 vector (nucleotides 2599–3132) is replaced by the DNA sequence encoding human MIF, Genbank Accession No. M25639, nucleotides 51 to 397. The thioredoxin/MIF fusion gene is expressed under the conditions described for the thioredoxin/IL-11 in Example 2. The culture growth temperature used in this case is 37° C. Under these conditions the majority of the thioredoxin/MIF fusion protein accumulates in the soluble cellular fraction. The fusion protein can be cleaved using the enterokinase treatment described in Example 2.

EXAMPLE 12

Thioredoxin/Small Peptide Fusion Molecules

Native *E. coli* thioredoxin can be expressed at high levels in *E. coli* using strain GI724 containing the same plasmid expression vector described in Example 3 deleted for nucleotides 2569–3129, and employing the growth and induction protocol outlined in Example 2. Under these conditions thioredoxin accumulated to approximately 10% of the total protein, all of it in the soluble cellular fraction.

FIG. 4 illustrates insertion of 13 amino acid residues encoding an enterokinase cleavage site into the active-site loop of thioredoxin, between residues $G_{34}$ and $P_{35}$ of the thioredoxin protein sequence. The fusion protein containing this internal enterokinase site was expressed at levels equivalent to native thioredoxin, and was cleaved with an enterokinase treatment as outlined in Example 2 above. The fusion protein was found to be as stable as native thioredoxin to heat treatments, being resistant to a 10 minute incubation at 80° C. as described in Example 3.

Below are listed twelve additional peptide insertions which were also made into the active-site loop of thioredoxin between $G_3$ and $P_{35}$. The sequences are each 14 amino acid residues in length and are random in composition. Each of the thioredoxin fusion proteins containing these random insertions were made at levels comparable to native thioredoxin. All of them were found in the soluble cellular fraction. These peptides include the following sequences:

Pro-Leu-Gln-Arg-Ile-Pro-Pro-Gln-Ala-Leu-Arg-Val-Glu-Gly (SEQ ID NO:1),
Pro-Arg-Asp-Cys-Val-Gln-Arg-Gly-Lys-Ser-Leu-Ser-Leu-Gly (SEQ ID NO:2),
Pro-Met-Arg-His-Asp-Val-Arg-Cys-Val-Leu-His-Gly-Thr-Gly (SEQ ID NO:3),
Pro-Gly-Val-Arg-Leu-Pro-Ile-Cys-Tyr-Asp-Asp-Ile-Arg-Gly (SEQ ID NO:4),
Pro-Lys-Phe-Ser-Asp-Gly-Ala-Gln-Gly-Leu-Gly-Ala-Val-Gly (SEQ ID NO:5),
Pro-Pro-Ser-Leu-Val-Gln-Asp-Asp-Ser-Phe-Glu-Asp-Arg-Gly (SEQ ID NO:6),
Pro-Trp-Ile-Asn-Gly-Ala-Thr-Pro-Val-Lys-Ser-Ser-Ser-Gly (SEQ ID NO:7),
Pro-Ala-His-Arg-Phe-Arg-Gly-Gly-Ser-Pro-Ala-Ile-Phe-Gly (SEQ ID NO:8),
Pro-Ile-Met-Gly-Ala-Ser-His-Gly-Glu-Arg-Gly-Pro-Glu-Gly (SEQ ID NO:9),
Pro-Asp-Ser-Leu-Arg-Arg-Arg-Glu-Gly-Phe-Gly-Leu-Leu-Gly (SEQ ID NO:10),
Pro-Ser-Glu-Tyr-Pro-Gly-Leu-Ala-Thr-Gly-His-His-Val-Gly (SEQ ID NO:11),
and Pro-Leu-Gly-Val-Leu-Gly-Ser-Ile-Trp-Leu-Glu-Arg-Gln-Gly (SEQ ID NO:12).

The inserted sequences contained examples that were both hydrophobic and hydrophilic, and examples that contained cysteine residues. It appears that the active-site loop of thioredoxin can tolerate a wide variety of peptide insertions resulting in soluble fusion proteins. Standard procedures can be used to purify these loop "inserts".

EXAMPLE 13

Human Interleukin-6

Human interleukin-6 (IL-6) is be expressed at high levels in *E. coli* as a thioredoxin fusion protein using an expression vector similar to modified pALtrxA/EK/IL-11ΔPro-581 described in Example 3 above. To express a thioredoxin/IL-6 fusion, the DNA sequence in modified pALtrxA/EK/IL-11ΔPro-581 encoding human IL-11 (nucleotides 2599–3132) is replaced by the 561 nucleotide DNA sequence (SEQ ID NO:19) shown in FIG. 6 encoding full-length, mature human IL-6 [Hirano et al, Nature 324:73–76 (1986)]. The host strain and expression protocol used for the production of thioredoxin/IL-6 fusion protein are as described in Example 2.

When the fusion protein was synthesized at 37° C., approximately 50% of it was found in the "inclusion body" or insoluble fraction. However all of the thioredoxin/IL-6 fusion protein, representing up to 10% of the total cellular protein, was found in the soluble fraction when the temperature of synthesis was lowered to 25° C.

EXAMPLE 14

Human Macrophage Colony Stimulating Factor

Human Macrophage Colony Stimulating Factor (M-CSF) can be expressed at high levels in *E. coli* as a thioredoxin fusion protein using the modified expression vector similar to pALtrx/EK/IL-11ΔPro581 described in Example 3 above.

The DNA sequence encoding human IL-11 in modified pALtrxA/EK/IL-11ΔPro-581 (nucleotides 2599–3135) is replaced by the 669 nucleotide DNA sequence shown in FIG. 7 encoding the first 223 amino acids of mature human M-CSFβ [G. G. Wong et al., Science 235:1504–1508 (1987)]. The host strain and expression protocol used for the production of thioredoxin/M-CSF fusion protein was as described in Example 2 above.

As was seen with the thioredoxin/IL-11 fusion protein, all of the thioredoxin/M-CSF fusion protein was found in the soluble cellular fraction, representing up to 10% of the total protein.

EXAMPLE 15

Release of Fusion Protein via Osmotic Shock

To determine whether or not the fusions of heterologous proteins to thioredoxin according to this invention enable targeting to the host cell's adhesion sites and permit the release of the fusion proteins from the cell, the cells were exposed to simple osmotic shock and freeze/thaw procedures.

Cells overproducing wild-type *E. coli* thioredoxin, human thioredoxin, the *E. coli* thioredoxin-MIP-1α fusion or the *E. coli* thioredoxin/IL-11 fusion were used in the following procedures.

For an osmotic shock treatment, cells were resuspended at 2 $A_{550}$/ml in 20 mM Tris-Cl pH 8.0/2.5 mM EDTA/20% w/v sucrose and kept cold on ice for 10 minutes. The cells were then pelleted by centrifugation (12,000×g, 30 seconds) and gently resuspended in the same buffer as above but with sucrose omitted. After an additional 10 minute period on ice, to allow for the osmotic release of proteins, cells were re-pelleted by centrifugation (12,000×g, 2 minutes) and the supernatant ("shockate") examined for its protein content. Wild-type *E. coli* thioredoxin and human thioredoxin were quantitatively released, giving "shockate" preparations which were >80% pure thioredoxin. More significantly >80% of the thioredoxin-MIP-1α and >50% of the thioredoxin/IL-11 fusion proteins were released by this osmotic treatment.

A simple freeze/thaw procedure produced similar results, releasing thioredoxin fusion proteins selectively, while leaving most of the other cellular proteins inside the cell. A typical freeze/thaw procedure entails resuspending cells at 2 $A_{550}$/ml in 20 mM Tris-Cl pH 8.0/2.5 mM EDTA and quickly freezing the suspension in dry ice or liquid nitrogen. The frozen suspension is then allowed to slowly thaw before spinning out the cells (12,000×g, 2 minutes) and examining the supernatant for protein.

Although the resultant "shockate" may require additional purification, the initial "shockate" is characterized by the absence of nucleic acid contaminants. Thus, compared to an initial lysate, the purity of the "shockate" is significantly better, and does not require the difficult removal of DNA from bacterial lysates. Fewer additional steps should be required for total purity of the "shockate".

EXAMPLE 16

Preparation of Modified Thioredoxin-Like Variants with Affinity for Immobilized Metal Ions To improve the purification process, a modified thioredoxin-like sequence is prepared to include metal-binding/chelating amino acids; the preparation involves the replacement of three residues of the natural *E. coli* thioredoxin amino-acid sequence as encoded in the expression vector pALtrxA/EK/IL-11ΔPro-581 (specifically serine 2, glutamate 31 and glutamine 63) with histidine residues. The changes are made in the DNA encoding thioredoxin using standard DNA manipulation techniques, described extensively by Sambrook, Fritsch and Maniatis, in "Molecular Cloning, a Laboratory Manual", 2nd edition, Cold Spring Harbor Laboratory, Cold Spring Harbor, N.Y. (1989). The codon changes in thioredoxin are AGT→CAT (Ser 2→His 2), GAG→CAC (Glu 31→His 31) and CAA→CAC (Gln 63→His 63). The modified thioredoxin/IL-11 variant carrying the three extra histidine residues is named "his-patch thioredoxin/IL-11", and the new expression plasmid called pHPTrxF-EKILdp781. The sequence is set forth in FIG. 7 (SEQ ID NO:25). Several additional changes are also incorporated into the thioredoxin sequences in this vector in an effort to enhance expression by changing to certain *E. coli* preference codons, e.g., at residue numbers 3, 7, 10, 11, 12, 14, 15, 18–23, 25, 26, 40 and 65 in thioredoxin, yet without altering the amino-acids encoded. The ribosome-binding sequence immediately upstream of the fusion gene in pHPTrxF-EKIL11dp-781 is also changed relative to pALtrxA/EK/IL-11ΔPro-581 as is described in Example 3 for the thioredoxin/MIP-1α fusion.

Yet another modified thioredoxin/IL-11 variant, in this case having histidine replacements only at residues 31 and 63 of thioredoxin ("his-patch2 thioredoxin/IL-11") is prepared. This plasmid vector is designated as pHP2TrxF-EKIL11dp-781.

Production of "his-patch" or "his-patch2" thioredoxin/IL-11 fusion protein is achieved as is described for the wild-type thioredoxin/IL-11 fusion in Example 2. Thirty grams of cells containing either of the his-patch fusions are lysed in a French pressure cell in 20 mM Tris-Cl, pH 8 containing 1 mM p-aminobenzamidine and 1 mM phenyl-methylsulfonyl fluoride. The lysate is clarified by centrifugation at 15,000×g for 10 mins and the supernatant passed at 4° C. over a 300 ml column of QAE-Toyopearl previously equilibrated with lysis buffer. The flow through is discarded since at this stage all of the his-patch thioredoxin/IL-11 fusion binds to the column. The column is then washed with 600 ml of lysis buffer, followed by 600 ml of lysis buffer containing 1 mM EDTA, and then 3000 ml of lysis buffer again. (These washing steps remove any traces of bound metal from the fusion and greatly enhance the capacity of subsequent chelate-affinity columns. In some instances the binding to QAE-Toyopearl and washing with EDTA is omitted and the subsequent loss in chelate column capacity accepted). The fusion is eluted from the QAE-Toyopearl column with lysis buffer containing 200 mM NaCl. The eluted fraction containing the his-patch fusion is dialysed to remove any last traces of EDTA, first against 10 volumes of 50 mM sodium acetate, pH 5.0/200 mM NaCl, and then against a further 10 volumes of 50 mM Tris-Cl pH 7.0/200 mM NaCl.

A column of chelating-Sepharose FF is charged with nickel ions by passage of 10 column volumes of 20 mM nickel ammonium sulfate, followed by washing and equilibration with a further 25 column volumes of 200 mM NaCl, 50 mM Tris-Cl pH 7.0, 1 mM imidazole. The dialysed QAE eluate containing the his-patch fusion is passed over the column, which is then washed with 200 mM NaCl, 50 mM Tris-Cl pH 7.0, 1 mM imidazole until the absorbance at 280 nm falls below 0.05. Most remaining contaminants are removed at this stage. Purified fusion protein is then eluted by a step of 200 mM imidazole in the same buffer.

The method lends itself to be readily modified. Other metal ions in addition to nickel may be used including cobalt, copper and zinc. The buffer compositions may also be changed, with conditions selected empirically but usually maintaining pH in the range of pH 6.5–8.5 for good binding to chelate columns. Binding to these columns also occurs over a wide range of ionic strengths. Elution of the his-patch thioredoxin fusion can be achieved by step elution with imidazole, as described above, or by an imidazole gradient, or by competition with other chelating agents such as EDTA, or by a drop in pH, e.g., to pH 4. Other metal-chelate affinity matrices may also be used in substitution for chelating-Sepharose FF. Other column matrices employing the iminodiacetic acid (IDA) chelating group, or the nitrilo-triacetic acid (NTA) chelating group can be used.

In addition to the metal-chelate affinity purification step outlined above, the his-patch thioredoxin/IL-11 and his-patch2 thioredoxin/IL-11 fusions can also be selectively released from unlysed cells by the osmotic shock procedure of Example 15.

In addition, the fusion protein can be cleaved and the cleavage products, e.g., the modified thioredoxin and the protein of interest, can be readily separated from each other utilizing the same methods outlined for purification of the fusion protein.

Numerous modifications and variations of the present invention are included in the aboveidentified specification and are expected to be obvious to one of skill in the art. Such modifications and alterations to the compositions and processes of the present invention are believed to be encompassed in the scope of the claims appended hereto.

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 14 amino acids
      (B) TYPE: amino acid
      (C) STRANDEDNESS: double
      (D) TOPOLOGY: unknown

```
       (ii) MOLECULE TYPE: peptide (xi) SEQUENCE DESCRIPTION: SEQ ID NO:1:

Pro Leu Gln Arg Ile Pro Pro Gln Ala Leu Arg Val Glu Gly
       1               5                  10

(2) INFORMATION FOR SEQ ID NO:2:

(i) SEQUENCE CHARACTERISTICS:
           (A) LENGTH: 14 amino acids
           (B) TYPE: amino acid
           (C) STRANDEDNESS: double
           (D) TOPOLOGY: unknown (ii) MOLECULE TYPE: peptide (xi) SEQUENCE DESCRIPTION: SEQ ID NO:2:

Pro Arg Asp Cys Val Gln Arg Gly Lys Ser Leu Ser Leu Gly
       1               5                  10

(2) INFORMATION FOR SEQ ID NO:3:

(i) SEQUENCE CHARACTERISTICS:
           (A) LENGTH: 14 amino acids
           (B) TYPE: amino acid
           (C) STRANDEDNESS: double
           (D) TOPOLOGY: unknown (ii) MOLECULE TYPE: peptide (xi) SEQUENCE DESCRIPTION: SEQ ID NO:3:

Pro Met Arg His Asp Val Arg Cys Val Leu His Gly Thr Gly
       1               5                  10

(2) INFORMATION FOR SEQ ID NO:4:

(i) SEQUENCE CHARACTERISTICS:
           (A) LENGTH: 14 amino acids
           (B) TYPE: amino acid
           (C) STRANDEDNESS: double
           (D) TOPOLOGY: unknown (ii) MOLECULE TYPE: peptide (xi) SEQUENCE DESCRIPTION: SEQ ID NO:4:

Pro Gly Val Arg Leu Pro Ile Cys Tyr Asp Asp Ile Arg Gly
       1               5                  10

(2) INFORMATION FOR SEQ ID NO:5:

(i) SEQUENCE CHARACTERISTICS:
           (A) LENGTH: 14 amino acids
           (B) TYPE: amino acid
           (C) STRANDEDNESS: double
           (D) TOPOLOGY: unknown (ii) MOLECULE TYPE: peptide (xi) SEQUENCE DESCRIPTION: SEQ ID NO:5:

Pro Lys Phe Ser Asp Gly Ala Gln Gly Leu Gly Ala Val Gly
       1               5                  10

(2) INFORMATION FOR SEQ ID NO:6:

(i) SEQUENCE CHARACTERISTICS:
           (A) LENGTH: 14 amino acids
           (B) TYPE: amino acid
           (C) STRANDEDNESS: double
           (D) TOPOLOGY: unknown
```

(ii) MOLECULE TYPE: peptide (xi) SEQUENCE DESCRIPTION: SEQ ID NO:6:

Pro Pro Ser Leu Val Gln Asp Asp Ser Phe Glu Asp Arg Gly
    1               5                   10

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: double
        (D) TOPOLOGY: unknown (ii) MOLECULE TYPE: peptide (xi) SEQUENCE DESCRIPTION: SEQ ID NO:7:

Pro Trp Ile Asn Gly Ala Thr Pro Val Lys Ser Ser Ser Gly
    1               5                   10

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: double
        (D) TOPOLOGY: unknown (ii) MOLECULE TYPE: peptide (xi) SEQUENCE DESCRIPTION: SEQ ID NO:8:

Pro Ala His Arg Phe Arg Gly Gly Ser Pro Ala Ile Phe Gly
    1               5                   10

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS: double
        (D) TOPOLOGY: unknown (ii) MOLECULE TYPE: peptide (xi) SEQUENCE DESCRIPTION: SEQ ID NO:9:

Pro Ile Met Gly Ala Ser His Gly Glu Arg Gly Pro Glu Gly
    1               5                   10

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: double
        (D) TOPOLOGY: unknown (ii) MOLECULE TYPE: peptide (xi) SEQUENCE DESCRIPTION: SEQ ID NO:10:

Pro Asp Ser Leu Arg Arg Arg Glu Gly Phe Gly Leu Leu Gly
    1               5                   10

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: double (D) TOPOLOGY: unknown (ii) MOLECULE TYPE: peptide (xi) SEQUENCE DESCRIPTION: SEQ ID NO:11:

Pro Ser Glu Tyr Pro Gly Leu Ala Thr Gly His His Val Gly
    1               5                   10

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: double
        (D) TOPOLOGY: unknown (ii) MOLECULE TYPE: peptide (xi) SEQUENCE DESCRIPTION: SEQ ID NO:12:

Pro Leu Gly Val Leu Gly Ser Ile Trp Leu Glu Arg Gln
    1               5                   10

(2) INFORMATION FOR SEQ ID NO:13:

(i) SEQUENCE CHARACTERISTICS:
        (A) LENGTH: 3632 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 2242..3132

(xi) SEQUENCE DESCRIPTION: SEQ ID NO:13:

| | | |
|---|---|---|
| GACGAAAGGG CCTCGTGATA CGCCTATTTT TATAGGTTAA TGTCATGATA ATAATGGTTT | 60 |
| CTTAGACGTC AGGTGGCACT TTTCGGGGAA ATGTGCGCGG AACCCCTATT TGTTTATTTT | 120 |
| TCTAAATACA TTCAAATATG TATCCGCTCA TGAGACAATA ACCCTGATAA ATGCTTCAAT | 180 |
| AATATTGAAA AAGGAAGAGT ATGAGTATTC AACATTTCCG TGTCGCCCTT ATTCCCTTTT | 240 |
| TTGCGGCATT TTGCCTTCCT GTTTTTGCTC ACCCAGAAAC GCTGGTGAAA GTAAAAGATG | 300 |
| CTGAAGATCA GTTGGGTGCA CGAGTGGGTT ACATCGAACT GGATCTCAAC AGCGGTAAGA | 360 |
| TCCTTGAGAG TTTTCGCCCC GAAGAACGTT TTCCAATGAT GAGCACTTTT AAAGTTCTGC | 420 |
| TATGTGGCGC GGTATTATCC CGTATTGACG CCGGGCAAGA GCAACTCGGT CGCCGCATAC | 480 |
| ACTATTCTCA GAATGACTTG GTTGAGTACT CACCAGTCAC AGAAAAGCAT CTTACGGATG | 540 |
| GCATGACAGT AAGAGAATTA TGCAGTGCTG CCATAACCAT GAGTGATAAC ACTGCGGCCA | 600 |
| ACTTACTTCT GACAACGATC GGAGGACCGA AGGAGCTAAC CGCTTTTTTG CACAACATGG | 660 |
| GGGATCATGT AACTCGCCTT GATCGTTGGG AACCGGAGCT GAATGAAGCC ATACCAAACG | 720 |
| ACGAGCGTGA CACCACGATG CCTGTAGCAA TGGCAACAAC GTTGCGCAAA CTATTAACTG | 780 |
| GCGAACTACT TACTCTAGCT TCCCGGCAAC AATTAATAGA CTGGATGGAG GCGGATAAAG | 840 |
| TTGCAGGACC ACTTCTGCGC TCGGCCCTTC CGGCTGGCTG GTTTATTGCT GATAAATCTG | 900 |
| GAGCCGGTGA GCGTGGGTCT CGCGGTATCA TTGCAGCACT GGGGCCAGAT GGTAAGCCCT | 960 |
| CCCGTATCGT AGTTATCTAC ACGACGGGGA GTCAGGCAAC TATGGATGAA CGAAATAGAC | 1020 |
| AGATCGCTGA GATAGGTGCC TCACTGATTA AGCATTGGTA ACTGTCAGAC CAAGTTTACT | 1080 |
| CATATATACT TTAGATTGAT TTAAAACTTC ATTTTTAATT TAAAAGGATC TAGGTGAAGA | 1140 |

-continued

```
TCCTTTTTGA TAATCTCATG ACCAAAATCC CTTAACGTGA GTTTTCGTTC CACTGAGCGT      1200

CAGACCCCGT AGAAAAGATC AAAGGATCTT CTTGAGATCC TTTTTTTCTG CGCGTAATCT      1260

GCTGCTTGCA AACAAAAAAA CCACCGCTAC CAGCGGTGGT TTGTTTGCCG GATCAAGAGC      1320

TACCAACTCT TTTTCCGAAG GTAACTGGCT TCAGCAGAGC GCAGATACCA AATACTGTCC      1380

TTCTAGTGTA GCCGTAGTTA GGCCACCACT TCAAGAACTC TGTAGCACCG CCTACATACC      1440

TCGCTCTGCT AATCCTGTTA CCAGTGGCTG CTGCCAGTGG CGATAAGTCG TGTCTTACCG      1500

GGTTGGACTC AAGACGATAG TTACCGGATA AGGCGCAGCG GTCGGGCTGA ACGGGGGGTT      1560

CGTGCACACA GCCCAGCTTG GAGCGAACGA CCTACACCGA ACTGAGATAC CTACAGCGTG      1620

AGCATTGAGA AAGCGCCACG CTTCCCGAAG GGAGAAAGGC GGACAGGTAT CCGGTAAGCG      1680

GCAGGGTCGG AACAGGAGAG CGCACGAGGG AGCTTCCAGG GGGAAACGCC TGGTATCTTT      1740

ATAGTCCTGT CGGGTTTCGC CACCTCTGAC TTGAGCGTCG ATTTTTGTGA TGCTCGTCAG      1800

GGGGGCGGAG CCTATGGAAA AACGCCAGCA ACGCGGCCTT TTTACGGTTC CTGGCCTTTT      1860

GCTGGCCTTT TGCTCACATG TTCTTTCCTG CGTTATCCCC TGATTCTGTG ATAACCGTA      1920

TTACCGCCTT TGAGTGAGCT GATACCGCTC GCCGCAGCCG AACGACCGAG CGCAGCGAGT      1980

CAGTGAGCGA GGAAGCGGAA GAGCGCCCAA TACGCAAACC GCCTCTCCCC GCGCGTTGGC      2040

CGATTCATTA ATGCAGAATT GATCTCTCAC CTACCAAACA ATGCCCCCCT GCAAAAAATA      2100

AATTCATATA AAAAACATAC AGATAACCAT CTGCGGTGAT AAATTATCTC TGGCGGTGTT      2160

GACATAAATA CCACTGGCGG TGATACTGAG CACATCAGCA GGACGCACTG ACCACCATGA      2220

ATTCAAGAAG GAGATATACA T ATG AGC GAT AAA ATT ATT CAC CTG ACT GAC       2271
                         Met Ser Asp Lys Ile Ile His Leu Thr Asp
                           1               5                  10

GAC AGT TTT GAC ACG GAT GTA CTC AAA GCG GAC GGG GCG ATC CTC GTC       2319
Asp Ser Phe Asp Thr Asp Val Leu Lys Ala Asp Gly Ala Ile Leu Val
             15                  20                  25

GAT TTC TGG GCA GAG TGG TGC GGT CCG TGC AAA ATG ATC GCC CCG ATT       2367
Asp Phe Trp Ala Glu Trp Cys Gly Pro Cys Lys Met Ile Ala Pro Ile
         30                  35                  40

CTG GAT GAA ATC GCT GAC GAA TAT CAG GGC AAA CTG ACC GTT GCA AAA       2415
Leu Asp Glu Ile Ala Asp Glu Tyr Gln Gly Lys Leu Thr Val Ala Lys
     45                  50                  55

CTG AAC ATC GAT CAA AAC CCT GGC ACT GCG CCG AAA TAT GGC ATC CGT       2463
Leu Asn Ile Asp Gln Asn Pro Gly Thr Ala Pro Lys Tyr Gly Ile Arg
 60                  65                  70

GGT ATC CCG ACT CTG CTG CTG TTC AAA AAC GGT GAA GTG GCG GCA ACC       2511
Gly Ile Pro Thr Leu Leu Leu Phe Lys Asn Gly Glu Val Ala Ala Thr
 75                  80                  85                  90

AAA GTG GGT GCA CTG TCT AAA GGT CAG TTG AAA GAG TTC CTC GAC GCT       2559
Lys Val Gly Ala Leu Ser Lys Gly Gln Leu Lys Glu Phe Leu Asp Ala
                 95                 100                 105

AAC CTG GCC GGT TCT GGT TCT GGT GAT GAC GAT GAC AAA GGT CCA CCA       2607
Asn Leu Ala Gly Ser Gly Ser Gly Asp Asp Asp Asp Lys Gly Pro Pro
             110                 115                 120

CCA GGT CCA CCT CGA GTT TCC CCA GAC CCT CGG GCC GAG CTG GAC AGC       2655
Pro Gly Pro Pro Arg Val Ser Pro Asp Pro Arg Ala Glu Leu Asp Ser
         125                 130                 135

ACC GTG CTC CTG ACC CGC TCT CTC CTG GCG GAC ACG CGG CAG CTG GCT       2703
Thr Val Leu Leu Thr Arg Ser Leu Leu Ala Asp Thr Arg Gln Leu Ala
     140                 145                 150

GCA CAG CTG AGG GAC AAA TTC CCA GCT GAC GGG GAC CAC AAC CTG GAT       2751
```

```
Ala Gln Leu Arg Asp Lys Phe Pro Ala Asp Gly Asp His Asn Leu Asp
155                 160                 165                 170

TCC CTG CCC ACC CTG GCC ATG AGT GCG GGG GCA CTG GGA GCT CTA CAG      2799
Ser Leu Pro Thr Leu Ala Met Ser Ala Gly Ala Leu Gly Ala Leu Gln
                175                 180                 185

CTC CCA GGT GTG CTG ACA AGG CTG CGA GCG GAC CTA CTG TCC TAC CTG      2847
Leu Pro Gly Val Leu Thr Arg Leu Arg Ala Asp Leu Leu Ser Tyr Leu
            190                 195                 200

CGG CAC GTG CAG TGG CTG CGC CGG GCA GGT GGC TCT TCC CTG AAG ACC      2895
Arg His Val Gln Trp Leu Arg Arg Ala Gly Gly Ser Ser Leu Lys Thr
        205                 210                 215

CTG GAG CCC GAG CTG GGC ACC CTG CAG GCC CGA CTG GAC CGG CTG CTG      2943
Leu Glu Pro Glu Leu Gly Thr Leu Gln Ala Arg Leu Asp Arg Leu Leu
    220                 225                 230

CGC CGG CTG CAG CTC CTG ATG TCC CGC CTG GCC CTG CCC CAG CCA CCC      2991
Arg Arg Leu Gln Leu Leu Met Ser Arg Leu Ala Leu Pro Gln Pro Pro
235                 240                 245                 250

CCG GAC CCG CCG GCG CCC CCG CTG GCG CCC CCC TCC TCA GCC TGG GGG      3039
Pro Asp Pro Pro Ala Pro Pro Leu Ala Pro Pro Ser Ser Ala Trp Gly
                255                 260                 265

GGC ATC AGG GCC GCC CAC GCC ATC CTG GGG GGG CTG CAC CTG ACA CTT      3087
Gly Ile Arg Ala Ala His Ala Ile Leu Gly Gly Leu His Leu Thr Leu
            270                 275                 280

GAC TGG GCC GTG AGG GGA CTG CTG CTG CTG AAG ACT CGG CTG TGAAAGCTTA   3139
Asp Trp Ala Val Arg Gly Leu Leu Leu Leu Lys Thr Arg Leu
        285                 290                 295

TCGATACCGT CGACCTGCAG TAATCGTACA GGGTAGTACA AATAAAAAAG GCACGTCAGA    3199

TGACGTGCCT TTTTTCTTGT GAGCAGTAAG CTTGGCACTG GCCGTCGTTT TACAACGTCG    3259

TGACTGGGAA AACCCTGGCG TTACCCAACT TAATCGCCTT GCAGCACATC CCCCTTTCGC    3319

CAGCTGGCGT AATAGCGAAG AGGCCCGCAC CGATCGCCCT TCCCAACAGT TGCGCAGCCT    3379

GAATGGCGAA TGGCGCCTGA TGCGGTATTT TCTCCTTACG CATCTGTGCG GTATTTCACA    3439

CCGCATATAT GGTGCACTCT CAGTACAATC TGCTCTGATG CCGCATAGTT AAGCCAGCCC    3499

CGACACCCGC CAACACCCGC TGACGCGCCC TGACGGGCTT GTCTGCTCCC GGCATCCGCT    3559

TACAGACAAG CTGTGACCGT CTCCGGGAGC TGCATGTGTC AGAGGTTTTC ACCGTCATCA    3619

CCGAAACGCG CGA                                                       3632

(2) INFORMATION FOR SEQ ID NO:14:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO:14:

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80
```

```
Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly Asp Asp Asp Lys Gly Pro Pro Gly Pro Pro Arg Val
            115                 120                 125

Ser Pro Asp Pro Arg Ala Glu Leu Asp Ser Thr Val Leu Leu Thr Arg
            130                 135                 140

Ser Leu Leu Ala Asp Thr Arg Gln Leu Ala Ala Gln Leu Arg Asp Lys
145                 150                 155                 160

Phe Pro Ala Asp Gly Asp His Asn Leu Asp Ser Leu Pro Thr Leu Ala
                165                 170                 175

Met Ser Ala Gly Ala Leu Gly Ala Leu Gln Leu Pro Gly Val Leu Thr
                180                 185                 190

Arg Leu Arg Ala Asp Leu Leu Ser Tyr Leu Arg His Val Gln Trp Leu
                195                 200                 205

Arg Arg Ala Gly Gly Ser Ser Leu Lys Thr Leu Glu Pro Glu Leu Gly
            210                 215                 220

Thr Leu Gln Ala Arg Leu Asp Arg Leu Leu Arg Arg Leu Gln Leu Leu
225                 230                 235                 240

Met Ser Arg Leu Ala Leu Pro Gln Pro Pro Asp Pro Pro Ala Pro
                245                 250                 255

Pro Leu Ala Pro Pro Ser Ser Ala Trp Gly Gly Ile Arg Ala Ala His
                260                 265                 270

Ala Ile Leu Gly Gly Leu His Leu Thr Leu Asp Trp Ala Val Arg Gly
            275                 280                 285

Leu Leu Leu Leu Lys Thr Arg Leu
290                 295

(2) INFORMATION FOR SEQ ID NO:15:

(i) SEQUENCE CHARACTERISTICS:
        (A) LENGTH: 213 base pairs
        (B) TYPE: nucleic acid
        (C) STRANDEDNESS: double
        (D) TOPOLOGY: unknown (ii) MOLECULE TYPE: DNA (ix) FEATURE:
         (A) NAME/KEY: CDS
         (B) LOCATION: 1..210

(xi) SEQUENCE DESCRIPTION: SEQ ID NO:15:

GCA CCA CTT GCT GCT GAC ACG CCG ACC GCC TGC TGC TTC AGC TAC ACC         48
Ala Pro Leu Ala Ala Asp Thr Pro Thr Ala Cys Cys Phe Ser Tyr Thr
 1               5                  10                  15

TCC CGA CAG ATT CCA CAG AAT TTC ATA GCT GAC TAC TTT GAG ACG AGC         96
Ser Arg Gln Ile Pro Gln Asn Phe Ile Ala Asp Tyr Phe Glu Thr Ser
                20                  25                  30

AGC CAG TGC TCC AAG CCC AGT GTC ATC TTC CTA ACC AAG AGA GGC CGG        144
Ser Gln Cys Ser Lys Pro Ser Val Ile Phe Leu Thr Lys Arg Gly Arg
            35                  40                  45

CAG GTC TGT GCT GAC CCC AGT GAG GAG TGG GTC CAG AAA TAC GTC AGT        192
Gln Val Cys Ala Asp Pro Ser Glu Glu Trp Val Gln Lys Tyr Val Ser
 50                 55                  60

GAC CTG GAG CTG AGT GCC TAA                                            213
Asp Leu Glu Leu Ser Ala
 65                 70
```

(2) INFORMATION FOR SEQ ID NO:16:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:16:

```
Ala Pro Leu Ala Ala Asp Thr Pro Thr Ala Cys Cys Phe Ser Tyr Thr
 1               5                  10                  15

Ser Arg Gln Ile Pro Gln Asn Phe Ile Ala Asp Tyr Phe Glu Thr Ser
                20                  25                  30

Ser Gln Cys Ser Lys Pro Ser Val Ile Phe Leu Thr Lys Arg Gly Arg
            35                  40                  45

Gln Val Cys Ala Asp Pro Ser Glu Glu Trp Val Gln Lys Tyr Val Ser
        50                  55                  60

Asp Leu Glu Leu Ser Ala
 65                  70
```

(2) INFORMATION FOR SEQ ID NO:17:

(i) SEQUENCE CHARACTERISTICS:
        (A) LENGTH: 345 base pairs
        (B) TYPE: nucleic acid
        (C) STRANDEDNESS: double
        (D) TOPOLOGY: unknown (ii) MOLECULE TYPE: DNA (ix) FEATURE:
        (A) NAME/KEY: CDS
        (B) LOCATION: 1..342

(xi) SEQUENCE DESCRIPTION: SEQ ID NO:17:

```
CAA GCT AAA CAT AAA CAA CGT AAA CGT CTG AAA TCT AGC TGT AAG AGA        48
Gln Ala Lys His Lys Gln Arg Lys Arg Leu Lys Ser Ser Cys Lys Arg
 1               5                  10                  15

CAC CCT TTG TAC GTG GAC TTC AGT GAC GTG GGG TGG AAT GAC TGG ATT        96
His Pro Leu Tyr Val Asp Phe Ser Asp Val Gly Trp Asn Asp Trp Ile
                20                  25                  30

GTG GCT CCC CCG GGG TAT CAC GCC TTT TAC TGC CAC GGA GAA TGC CCT       144
Val Ala Pro Pro Gly Tyr His Ala Phe Tyr Cys His Gly Glu Cys Pro
            35                  40                  45

TTT CCT CTG GCT GAT CAT CTG AAC TCC ACT AAT CAT GCC ATT GTT CAG       192
Phe Pro Leu Ala Asp His Leu Asn Ser Thr Asn His Ala Ile Val Gln
        50                  55                  60

ACG TTG GTC AAC TCT GTT AAC TCT AAG ATT CCT AAG GCA TGC TGT GTC       240
Thr Leu Val Asn Ser Val Asn Ser Lys Ile Pro Lys Ala Cys Cys Val
 65                  70                  75                  80

CCG ACA GAA CTC AGT GCT ATC TCG ATG CTG TAC CTT GAC GAG AAT GAA       288
Pro Thr Glu Leu Ser Ala Ile Ser Met Leu Tyr Leu Asp Glu Asn Glu
                85                  90                  95

AAG GTT GTA TTA AAG AAC TAT CAG GAC ATG GTT GTG GAG GGT TGT GGG       336
Lys Val Val Leu Lys Asn Tyr Gln Asp Met Val Val Glu Gly Cys Gly
                100                 105                 110

TGT CGC TAG                                                           345
Cys Arg
```

(2) INFORMATION FOR SEQ ID NO:18:

(i) SEQUENCE CHARACTERISTICS:
    (A) LENGTH: 114 amino acids
    (B) TYPE: amino acid
    (D) TOPOLOGY: linear (ii) MOLECULE TYPE: protein (xi) SEQUENCE DESCRIPTION: SEQ ID NO:18:

```
Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg
```

(2) INFORMATION FOR SEQ ID NO:19:

(i) SEQUENCE CHARACTERISTICS:
    (A) LENGTH: 561 base pairs
    (B) TYPE: nucleic acid
    (C) STRANDEDNESS: double
    (D) TOPOLOGY: unknown (ii) MOLECULE TYPE: DNA (ix) FEATURE:
    (A) NAME/KEY: CDS
    (B) LOCATION: 1..558

(xi) SEQUENCE DESCRIPTION: SEQ ID NO:19:

```
ATG GCT CCA GTA CCT CCA GGT GAA GAT TCT AAA GAT GTA GCC GCC CCA      48
Met Ala Pro Val Pro Pro Gly Glu Asp Ser Lys Asp Val Ala Ala Pro
 1               5                  10                  15

CAC AGA CAG CCA CTC ACC TCT TCA GAA CGA ATT GAC AAA CAA ATT CGG      96
His Arg Gln Pro Leu Thr Ser Ser Glu Arg Ile Asp Lys Gln Ile Arg
            20                  25                  30

TAC ATC CTC GAC GGC ATC TCA GCC CTG AGA AAG GAG ACA TGT AAC AAG     144
Tyr Ile Leu Asp Gly Ile Ser Ala Leu Arg Lys Glu Thr Cys Asn Lys
        35                  40                  45

AGT AAC ATG TGT GAA AGC AGC AAA GAG GCA CTG GCA GAA AAC AAC CTG     192
Ser Asn Met Cys Glu Ser Ser Lys Glu Ala Leu Ala Glu Asn Asn Leu
    50                  55                  60

AAC CTT CCA AAG ATG GCT GAA AAA GAT GGA TGC TTC CAA TCT GGA TTC     240
Asn Leu Pro Lys Met Ala Glu Lys Asp Gly Cys Phe Gln Ser Gly Phe
65                  70                  75                  80

AAT GAG GAG ACT TGC CTG GTG AAA ATC ATC ACT GGT CTT TTG GAG TTT     288
Asn Glu Glu Thr Cys Leu Val Lys Ile Ile Thr Gly Leu Leu Glu Phe
                85                  90                  95

GAG GTA TAC CTA GAG TAC CTC CAG AAC AGA TTT GAG AGT AGT GAG GAA     336
Glu Val Tyr Leu Glu Tyr Leu Gln Asn Arg Phe Glu Ser Ser Glu Glu
            100                 105                 110

CAA GCC AGA GCT GTG CAG ATG AGT ACA AAA GTC CTG ATC CAG TTC CTG     384
Gln Ala Arg Ala Val Gln Met Ser Thr Lys Val Leu Ile Gln Phe Leu
```

| | | | | | | | | | | | | |
|---|---|---|---|---|---|---|---|---|---|---|---|---|
| | 115 | | | 120 | | | | 125 | | | | |
| CAG | AAA | AAG | GCA | AAG | AAT | CTA | GAT | GCA | ATA | ACC | ACC | CCT | GAC | CCA | ACC | 432 |
| Gln | Lys | Lys | Ala | Lys | Asn | Leu | Asp | Ala | Ile | Thr | Thr | Pro | Asp | Pro | Thr | |
| | 130 | | | | 135 | | | | | 140 | | | | | | |
| ACA | AAT | GCC | AGC | CTG | CTG | ACG | AAG | CTG | CAG | GCA | CAG | AAC | CAG | TGG | CTG | 480 |
| Thr | Asn | Ala | Ser | Leu | Leu | Thr | Lys | Leu | Gln | Ala | Gln | Asn | Gln | Trp | Leu | |
| 145 | | | | | 150 | | | | | 155 | | | | | 160 | |
| CAG | GAC | ATG | ACA | ACT | CAT | CTC | ATT | CTG | CGC | AGC | TTT | AAG | GAG | TTC | CTG | 528 |
| Gln | Asp | Met | Thr | Thr | His | Leu | Ile | Leu | Arg | Ser | Phe | Lys | Glu | Phe | Leu | |
| | | | | 165 | | | | | 170 | | | | | 175 | | |
| CAG | TCC | AGC | CTG | AGG | GCT | CTT | CGG | CAA | ATG | TAG | | | | | | 561 |
| Gln | Ser | Ser | Leu | Arg | Ala | Leu | Arg | Gln | Met | | | | | | | |
| | | | 180 | | | | | 185 | | | | | | | | |

(2) INFORMATION FOR SEQ ID NO:20:

(i) SEQUENCE CHARACTERISTICS:
        (A) LENGTH: 186 amino acids
        (B) TYPE: amino acid
        (D) TOPOLOGY: linear (ii) MOLECULE TYPE: protein (xi) SEQUENCE DESCRIPTION: SEQ ID NO:20:

| | | | | | | | | | | | |
|---|---|---|---|---|---|---|---|---|---|---|---|
| Met | Ala | Pro | Val | Pro | Pro | Gly | Glu | Asp | Ser | Lys | Asp | Val | Ala | Ala | Pro |
| 1 | | | | 5 | | | | | 10 | | | | | 15 | |
| His | Arg | Gln | Pro | Leu | Thr | Ser | Ser | Glu | Arg | Ile | Asp | Lys | Gln | Ile | Arg |
| | | | 20 | | | | | 25 | | | | | 30 | | |
| Tyr | Ile | Leu | Asp | Gly | Ile | Ser | Ala | Leu | Arg | Lys | Glu | Thr | Cys | Asn | Lys |
| | | 35 | | | | | 40 | | | | | 45 | | | |
| Ser | Asn | Met | Cys | Glu | Ser | Ser | Lys | Glu | Ala | Leu | Ala | Glu | Asn | Asn | Leu |
| 50 | | | | | 55 | | | | | 60 | | | | | |
| Asn | Leu | Pro | Lys | Met | Ala | Glu | Lys | Asp | Gly | Cys | Phe | Gln | Ser | Gly | Phe |
| 65 | | | | 70 | | | | | 75 | | | | | 80 | |
| Asn | Glu | Glu | Thr | Cys | Leu | Val | Lys | Ile | Ile | Thr | Gly | Leu | Leu | Glu | Phe |
| | | | | 85 | | | | | 90 | | | | | 95 | |
| Glu | Val | Tyr | Leu | Glu | Tyr | Leu | Gln | Asn | Arg | Phe | Glu | Ser | Ser | Glu | Glu |
| | | | 100 | | | | | 105 | | | | | 110 | | |
| Gln | Ala | Arg | Ala | Val | Gln | Met | Ser | Thr | Lys | Val | Leu | Ile | Gln | Phe | Leu |
| | | 115 | | | | | 120 | | | | | 125 | | | |
| Gln | Lys | Lys | Ala | Lys | Asn | Leu | Asp | Ala | Ile | Thr | Thr | Pro | Asp | Pro | Thr |
| | 130 | | | | 135 | | | | | 140 | | | | | |
| Thr | Asn | Ala | Ser | Leu | Leu | Thr | Lys | Leu | Gln | Ala | Gln | Asn | Gln | Trp | Leu |
| 145 | | | | | 150 | | | | | 155 | | | | | 160 |
| Gln | Asp | Met | Thr | Thr | His | Leu | Ile | Leu | Arg | Ser | Phe | Lys | Glu | Phe | Leu |
| | | | | 165 | | | | | 170 | | | | | 175 | |
| Gln | Ser | Ser | Leu | Arg | Ala | Leu | Arg | Gln | Met | | | | | | |
| | | | 180 | | | | | 185 | | | | | | | |

(2) INFORMATION FOR SEQ ID NO:21:

(i) SEQUENCE CHARACTERISTICS:
        (A) LENGTH: 327 base pairs
        (B) TYPE: nucleic acid
        (C) STRANDEDNESS: double
        (D) TOPOLOGY: unknown (ii) MOLECULE TYPE: DNA (ix) FEATURE:
        (A) NAME/KEY: CDS (B) LOCATION: 1..327

(xi) SEQUENCE DESCRIPTION: SEQ ID NO:21:

| | | | | | | | | | | | | | | | | |
|---|---|---|---|---|---|---|---|---|---|---|---|---|---|---|---|---|
| ATG | AGC | GAT | AAA | ATT | ATT | CAC | CTG | ACT | GAC | GAC | AGT | TTT | GAC | ACG | GAT | 48 |
| Met | Ser | Asp | Lys | Ile | Ile | His | Leu | Thr | Asp | Asp | Ser | Phe | Asp | Thr | Asp | |
| 1 | | | | 5 | | | | 10 | | | | | 15 | | | |
| GTA | CTC | AAA | GCG | GAC | GGG | GCG | ATC | CTC | GTC | GAT | TTC | TGG | GCA | GAG | TGG | 96 |
| Val | Leu | Lys | Ala | Asp | Gly | Ala | Ile | Leu | Val | Asp | Phe | Trp | Ala | Glu | Trp | |
| | | | 20 | | | | | 25 | | | | | 30 | | | |
| TGC | GGT | CCG | TGC | AAA | ATG | ATC | GCC | CCG | ATT | CTG | GAT | GAA | ATC | GCT | GAC | 144 |
| Cys | Gly | Pro | Cys | Lys | Met | Ile | Ala | Pro | Ile | Leu | Asp | Glu | Ile | Ala | Asp | |
| | | 35 | | | | | 40 | | | | | 45 | | | | |
| GAA | TAT | CAG | GGC | AAA | CTG | ACC | GTT | GCA | AAA | CTG | AAC | ATC | GAT | CAA | AAC | 192 |
| Glu | Tyr | Gln | Gly | Lys | Leu | Thr | Val | Ala | Lys | Leu | Asn | Ile | Asp | Gln | Asn | |
| | 50 | | | | | 55 | | | | | 60 | | | | | |
| CCT | GGC | ACT | GCG | CCG | AAA | TAT | GGC | ATC | CGT | GGT | ATC | CCG | ACT | CTG | CTG | 240 |
| Pro | Gly | Thr | Ala | Pro | Lys | Tyr | Gly | Ile | Arg | Gly | Ile | Pro | Thr | Leu | Leu | |
| 65 | | | | | 70 | | | | | 75 | | | | | 80 | |
| CTG | TTC | AAA | AAC | GGT | GAA | GTG | GCG | GCA | ACC | AAA | GTG | GGT | GCA | CTG | TCT | 288 |
| Leu | Phe | Lys | Asn | Gly | Glu | Val | Ala | Ala | Thr | Lys | Val | Gly | Ala | Leu | Ser | |
| | | | | 85 | | | | | 90 | | | | | 95 | | |
| AAA | GGT | CAG | TTG | AAA | GAG | TTC | CTC | GAC | GCT | AAC | CTG | GCC | | | | 327 |
| Lys | Gly | Gln | Leu | Lys | Glu | Phe | Leu | Asp | Ala | Asn | Leu | Ala | | | | |
| | | | 100 | | | | | 105 | | | | | | | | |

(2) INFORMATION FOR SEQ ID NO:22:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:22:

| | | | | | | | | | | | | | | | |
|---|---|---|---|---|---|---|---|---|---|---|---|---|---|---|---|
| Met | Ser | Asp | Lys | Ile | Ile | His | Leu | Thr | Asp | Asp | Ser | Phe | Asp | Thr | Asp |
| 1 | | | | 5 | | | | 10 | | | | | 15 | | |
| Val | Leu | Lys | Ala | Asp | Gly | Ala | Ile | Leu | Val | Asp | Phe | Trp | Ala | Glu | Trp |
| | | | 20 | | | | | 25 | | | | | 30 | | |
| Cys | Gly | Pro | Cys | Lys | Met | Ile | Ala | Pro | Ile | Leu | Asp | Glu | Ile | Ala | Asp |
| | | 35 | | | | | 40 | | | | | 45 | | | |
| Glu | Tyr | Gln | Gly | Lys | Leu | Thr | Val | Ala | Lys | Leu | Asn | Ile | Asp | Gln | Asn |
| | 50 | | | | | 55 | | | | | 60 | | | | |
| Pro | Gly | Thr | Ala | Pro | Lys | Tyr | Gly | Ile | Arg | Gly | Ile | Pro | Thr | Leu | Leu |
| 65 | | | | | 70 | | | | | 75 | | | | | 80 |
| Leu | Phe | Lys | Asn | Gly | Glu | Val | Ala | Ala | Thr | Lys | Val | Gly | Ala | Leu | Ser |
| | | | | 85 | | | | | 90 | | | | | 95 | |
| Lys | Gly | Gln | Leu | Lys | Glu | Phe | Leu | Asp | Ala | Asn | Leu | Ala | | | |
| | | | 100 | | | | | 105 | | | | | | | |

(2) INFORMATION FOR SEQ ID NO:23:

(i) SEQUENCE CHARACTERISTICS:
        (A) LENGTH: 669 base pairs
        (B) TYPE: nucleic acid
        (C) STRANDEDNESS: double
        (D) TOPOLOGY: unknown (ii) MOLECULE TYPE: DNA (ix) FEATURE:
        (A) NAME/KEY: CDS
        (B) LOCATION: 1..669

(xi) SEQUENCE DESCRIPTION: SEQ ID NO:23:

```
GAA GAA GTT TCT GAA TAT TGT AGC CAC ATG ATT GGG AGT GGA CAC CTG         48
Glu Glu Val Ser Glu Tyr Cys Ser His Met Ile Gly Ser Gly His Leu
 1               5                  10                  15

CAG TCT CTG CAG CGG CTG ATT GAC AGT CAG ATG GAG ACC TCG TGC CAA         96
Gln Ser Leu Gln Arg Leu Ile Asp Ser Gln Met Glu Thr Ser Cys Gln
             20                  25                  30

ATT ACA TTT GAG TTT GTA GAC CAG GAA CAG TTG AAA GAT CCA GTG TGC        144
Ile Thr Phe Glu Phe Val Asp Gln Glu Gln Leu Lys Asp Pro Val Cys
         35                  40                  45

TAC CTT AAG AAG GCA TTT CTC CTG GTA CAA GAC ATA ATG GAG GAC ACC        192
Tyr Leu Lys Lys Ala Phe Leu Leu Val Gln Asp Ile Met Glu Asp Thr
     50                  55                  60

ATG CGC TTC AGA GAT AAC ACC CCC AAT GCC ATC GCC ATT GTG CAG CTG        240
Met Arg Phe Arg Asp Asn Thr Pro Asn Ala Ile Ala Ile Val Gln Leu
 65                  70                  75                  80

CAG GAA CTC TCT TTG AGG CTG AAG AGC TGC TTC ACC AAG GAT TAT GAA        288
Gln Glu Leu Ser Leu Arg Leu Lys Ser Cys Phe Thr Lys Asp Tyr Glu
                 85                  90                  95

GAG CAT GAC AAG GCC TGC GTC CGA ACT TTC TAT GAG ACA CCT CTC CAG        336
Glu His Asp Lys Ala Cys Val Arg Thr Phe Tyr Glu Thr Pro Leu Gln
            100                 105                 110

TTG CTG GAG AAG GTC AAG AAT GTC TTT AAT GAA ACA AAG AAT CTC CTT        384
Leu Leu Glu Lys Val Lys Asn Val Phe Asn Glu Thr Lys Asn Leu Leu
        115                 120                 125

GAC AAG GAC TGG AAT ATT TTC AGC AAG AAC TGC AAC AAC AGC TTT GCT        432
Asp Lys Asp Trp Asn Ile Phe Ser Lys Asn Cys Asn Asn Ser Phe Ala
    130                 135                 140

GAA TGC TCC AGC CAA GAT GTG GTG ACC AAG CCT GAT TGC AAC TGC CTG        480
Glu Cys Ser Ser Gln Asp Val Val Thr Lys Pro Asp Cys Asn Cys Leu
145                 150                 155                 160

TAC CCC AAA GCC ATC CCT AGC AGT GAC CCG GCC TCT GTC TCC CCT CAT        528
Tyr Pro Lys Ala Ile Pro Ser Ser Asp Pro Ala Ser Val Ser Pro His
                165                 170                 175

CAG CCC CTC GCC CCC TCC ATG GCC CCT GTG GCT GGC TTG ACC TGG GAG        576
Gln Pro Leu Ala Pro Ser Met Ala Pro Val Ala Gly Leu Thr Trp Glu
            180                 185                 190

GAC TCT GAG GGA ACT GAG GGC AGC TCC CTC TTG CCT GGT GAG CAG CCC        624
Asp Ser Glu Gly Thr Glu Gly Ser Ser Leu Leu Pro Gly Glu Gln Pro
        195                 200                 205

CTG CAC ACA GTG GAT CCA GGC AGT GCC AAG CAG CGG CCA CCC AGG            669
Leu His Thr Val Asp Pro Gly Ser Ala Lys Gln Arg Pro Pro Arg
    210                 215                 220
```

(2) INFORMATION FOR SEQ ID NO:24:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO:24:

```
Glu Glu Val Ser Glu Tyr Cys Ser His Met Ile Gly Ser Gly His Leu
 1               5                  10                  15

Gln Ser Leu Gln Arg Leu Ile Asp Ser Gln Met Glu Thr Ser Cys Gln
             20                  25                  30

Ile Thr Phe Glu Phe Val Asp Gln Glu Gln Leu Lys Asp Pro Val Cys
         35                  40                  45
```

```
Tyr Leu Lys Lys Ala Phe Leu Leu Val Gln Asp Ile Met Glu Asp Thr
     50                  55                  60

Met Arg Phe Arg Asp Asn Thr Pro Asn Ala Ile Ala Ile Val Gln Leu
 65                  70                  75                  80

Gln Glu Leu Ser Leu Arg Leu Lys Ser Cys Phe Thr Lys Asp Tyr Glu
                 85                  90                  95

Glu His Asp Lys Ala Cys Val Arg Thr Phe Tyr Glu Thr Pro Leu Gln
             100                 105                 110

Leu Leu Glu Lys Val Lys Asn Val Phe Asn Glu Thr Lys Asn Leu Leu
         115                 120                 125

Asp Lys Asp Trp Asn Ile Phe Ser Lys Asn Cys Asn Asn Ser Phe Ala
130                 135                 140

Glu Cys Ser Ser Gln Asp Val Val Thr Lys Pro Asp Cys Asn Cys Leu
145                 150                 155                 160

Tyr Pro Lys Ala Ile Pro Ser Ser Asp Pro Ala Ser Val Ser Pro His
                 165                 170                 175

Gln Pro Leu Ala Pro Ser Met Ala Pro Val Ala Gly Leu Thr Trp Glu
             180                 185                 190

Asp Ser Glu Gly Thr Glu Gly Ser Ser Leu Leu Pro Gly Glu Gln Pro
         195                 200                 205

Leu His Thr Val Asp Pro Gly Ser Ala Lys Gln Arg Pro Pro Arg
210                 215                 220

(2) INFORMATION FOR SEQ ID NO:25:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1..330

(xi) SEQUENCE DESCRIPTION: SEQ ID NO:25:

ATG CAT GAT AAA ATT ATT CAT CTG ACT GAT GAT TCT TTT GAT ACT GAT        48
Met His Asp Lys Ile Ile His Leu Thr Asp Asp Ser Phe Asp Thr Asp
 1               5                  10                  15

GTA CTT AAG GCA GAT GGT GCA ATC CTG GTT GAT TTC TGG GCA CAC TGG        96
Val Leu Lys Ala Asp Gly Ala Ile Leu Val Asp Phe Trp Ala His Trp
             20                  25                  30

TGC GGT CCG TGC AAA ATG ATC GCT CCG ATT CTG GAT GAA ATC GCT GAC       144
Cys Gly Pro Cys Lys Met Ile Ala Pro Ile Leu Asp Glu Ile Ala Asp
 35                  40                  45

GAA TAT CAG GGC AAA CTG ACC GTT GCA AAA CTG AAC ATC GAT CAC AAC       192
Glu Tyr Gln Gly Lys Leu Thr Val Ala Lys Leu Asn Ile Asp His Asn
     50                  55                  60

CCG GGC ACT GCG CCG AAA TAT GGC ATC CGT GGT ATC CCG ACT CTG CTG       240
Pro Gly Thr Ala Pro Lys Tyr Gly Ile Arg Gly Ile Pro Thr Leu Leu
 65                  70                  75                  80

CTG TTC AAA AAC GGT GAA GTG GCG GCA ACC AAA GTG GGT GCA CTG TCT       288
Leu Phe Lys Asn Gly Glu Val Ala Ala Thr Lys Val Gly Ala Leu Ser
                 85                  90                  95

AAA GGT CAG TTG AAA GAG TTC CTC GAC GCT AAC CTG GCC TAG               330
Lys Gly Gln Leu Lys Glu Phe Leu Asp Ala Asn Leu Ala
             100                 105                 110
```

(2) INFORMATION FOR SEQ ID NO:26:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:26:

```
Met His Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala His Trp
             20                  25                  30

Cys Gly Pro Cys Lys Met Ile Ala Pro Ile Leu Asp Glu Ile Ala Asp
         35                  40                  45

Glu Tyr Gln Gly Lys Leu Thr Val Ala Lys Leu Asn Ile Asp His Asn
     50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala
                100                 105
```

(2) INFORMATION FOR SEQ ID NO:27:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: CDS
        (B) LOCATION: 1..330

(xi) SEQUENCE DESCRIPTION: SEQ ID NO:27:

```
ATG AGT GAT AAA ATT ATT CAT CTG ACT GAT GAT TCT TTT GAT ACT GAT      48
Met Ser Asp Lys Ile Ile His Leu Thr Asp Asp Ser Phe Asp Thr Asp
 1               5                  10                  15

GTA CTT AAG GCA GAT GGT GCA ATC CTG GTT GAT TTC TGG GCA CAC TGG      96
Val Leu Lys Ala Asp Gly Ala Ile Leu Val Asp Phe Trp Ala His Trp
             20                  25                  30

TGC GGT CCG TGC AAA ATG ATC GCT CCG ATT CTG GAT GAA ATC GCT GAC     144
Cys Gly Pro Cys Lys Met Ile Ala Pro Ile Leu Asp Glu Ile Ala Asp
         35                  40                  45

GAA TAT CAG GGC AAA CTG ACC GTT GCA AAA CTG AAC ATC GAT CAC AAC     192
Glu Tyr Gln Gly Lys Leu Thr Val Ala Lys Leu Asn Ile Asp His Asn
     50                  55                  60

CCG GGC ACT GCG CCG AAA TAT GGC ATC CGT GGT ATC CCG ACT CTG CTG     240
Pro Gly Thr Ala Pro Lys Tyr Gly Ile Arg Gly Ile Pro Thr Leu Leu
 65                  70                  75                  80

CTG TTC AAA AAC GGT GAA GTG GCG GCA ACC AAA GTG GGT GCA CTG TCT     288
Leu Phe Lys Asn Gly Glu Val Ala Ala Thr Lys Val Gly Ala Leu Ser
                 85                  90                  95

AAA GGT CAG TTG AAA GAG TTC CTC GAC GCT AAC CTG GCC TAG             330
Lys Gly Gln Leu Lys Glu Phe Leu Asp Ala Asn Leu Ala
                100                 105                 110
```

(2) INFORMATION FOR SEQ ID NO:28:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:28:

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala His Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp His Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105
```

(2) INFORMATION FOR SEQ ID NO:29:

(i) SEQUENCE CHARACTERISTICS:
        (A) LENGTH: 4114 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:29:

```
GACGAAAGGG CCTCGTGATA CGCCTATTTT TATAGGTTAA TGTCATGATA ATAATGGTTT      60
CTTAGACGTC AGGTGGCACT TTTCGGGGAA ATGTGCGCGG AACCCCTATT TGTTTATTTT     120
TCTAAATACA TTCAAATATG TATCCGCTCA TGAGACAATA ACCCTGATAA ATGCTTCAAT     180
AATATTGAAA AAGGAAGAGT ATGAGTATTC AACATTTCCG TGTCGCCCTT ATTCCCTTTT     240
TTGCGGCATT TGCCTTCCT GTTTTTGCTC ACCCAGAAAC GCTGGTGAAA GTAAAAGATG     300
CTGAAGATCA GTTGGGTGCA CGAGTGGGTT ACATCGAACT GGATCTCAAC AGCGGTAAGA     360
TCCTTGAGAG TTTTCGCCCC GAAGAACGTT TTCCAATGAT GAGCACTTTT AAAGTTCTGC     420
TATGTGGCGC GGTATTATCC CGTATTGACG CCGGGCAAGA GCAACTCGGT CGCCGCATAC     480
ACTATTCTCA GAATGACTTG GTTGAGTACT CACCAGTCAC AGAAAAGCAT CTTACGGATG     540
GCATGACAGT AAGAGAATTA TGCAGTGCTG CCATAACCAT GAGTGATAAC ACTGCGGCCA     600
ACTTACTTCT GACAACGATC GGAGGACCGA AGGAGCTAAC CGCTTTTTTG CACAACATGG     660
GGGATCATGT AACTCGCCTT GATCGTTGGG AACCGGAGCT GAATGAAGCC ATACCAAACG     720
ACGAGCGTGA CACCACGATG CCTGTAGCAA TGGCAACAAC GTTGCGCAAA CTATTAACTG     780
GCGAACTACT TACTCTAGCT TCCCGGCAAC AATTAATAGA CTGGATGGAG GCGGATAAAG     840
TTGCAGGACC ACTTCTGCGC TCGGCCCTTC CGGCTGGCTG GTTTATTGCT GATAAATCTG     900
GAGCCGGTGA GCGTGGGTCT CGCGGTATCA TTGCAGCACT GGGGCCAGAT GGTAAGCCCT     960
CCCGTATCGT AGTTATCTAC ACGACGGGGA GTCAGGCAAC TATGGATGAA CGAAATAGAC    1020
```

```
AGATCGCTGA GATAGGTGCC TCACTGATTA AGCATTGGTA ACTGTCAGAC CAAGTTTACT      1080

CATATATACT TTAGATTGAT TTAAAACTTC ATTTTTAATT TAAAAGGATC TAGGTGAAGA      1140

TCCTTTTTGA TAATCTCATG ACCAAAATCC CTTAACGTGA GTTTTCGTTC CACTGAGCGT      1200

CAGACCCCGT AGAAAAGATC AAAGGATCTT CTTGAGATCC TTTTTTTCTG CGCGTAATCT      1260

GCTGCTTGCA AACAAAAAAA CCACCGCTAC CAGCGGTGGT TTGTTTGCCG GATCAAGAGC      1320

TACCAACTCT TTTTCCGAAG GTAACTGGCT TCAGCAGAGC GCAGATACCA AATACTGTCC      1380

TTCTAGTGTA GCCGTAGTTA GGCCACCACT TCAAGAACTC TGTAGCACCG CCTACATACC      1440

TCGCTCTGCT AATCCTGTTA CCAGTGGCTG CTGCCAGTGG CGATAAGTCG TGTCTTACCG      1500

GGTTGGACTC AAGACGATAG TTACCGGATA AGGCGCAGCG GTCGGGCTGA ACGGGGGGTT      1560

CGTGCACACA GCCCAGCTTG GAGCGAACGA CCTACACCGA ACTGAGATAC CTACAGCGTG      1620

AGCATTGAGA AAGCGCCACG CTTCCCGAAG GGAGAAAGGC GGACAGGTAT CCGGTAAGCG      1680

GCAGGGTCGG AACAGGAGAG CGCACGAGGG AGCTTCCAGG GGGAAACGCC TGGTATCTTT      1740

ATAGTCCTGT CGGGTTTCGC CACCTCTGAC TTGAGCGTCG ATTTTTGTGA TGCTCGTCAG      1800

GGGGGCGGAG CCTATGGAAA AACGCCAGCA ACGCGGCCTT TTTACGGTTC CTGGCCTTTT      1860

GCTGGCCTTT TGCTCACATG TTCTTTCCTG CGTTATCCCC TGATTCTGTG ATAACCGTA      1920

TTACCGCCTT TGAGTGAGCT GATACCGCTC GCCGCAGCCG AACGACCGAG CGCAGCGAGT      1980

CAGTGAGCGA GGAAGCGGAA GAGCGCCCAA TACGCAAACC GCCTCTCCCC GCGCGTTGGC      2040

CGATTCATTA ATGCAGAATT GATCTCTCAC CTACCAAACA ATGCCCCCCT GCAAAAAATA      2100

AATTCATATA AAAAACATAC AGATAACCAT CTGCGGTGAT AAATTATCTC TGGCGGTGTT      2160

GACATAAATA CCACTGGCGG TGATACTGAG CACATCAGCA GGACGCACTG ACCACCATGA      2220

AGGTGACGCT CTTAAAAATT AAGCCCTGAA GAAGGGCAGC ATTCAAAGCA GAAGGCTTTG      2280

GGGTGTGTGA TACGAAACGA AGCATTGGCC GTAAGTGCGA TTCCGGATTA GCTGCCAATG      2340

TGCCAATCGC GGGGGGTTTT CGTTCAGGAC TACAACTGCC ACACACCACC AAAGCTAACT      2400

GACAGGAGAA TCCAGATGGA TGCACAAACA CGCCGCCGCG AACGTCGCGC AGAGAAACAG      2460

GCTCAATGGA AAGCAGCAAA TCCCCTGTTG GTTGGGGTAA GCGCAAAACC AGTTCCGAAA      2520

GATTTTTTTA ACTATAAACG CTGATGGAAG CGTTTATGCG GAAGAGGTAA AGCCCTTCCC      2580

GAGTAACAAA AAAACAACAG CATAAATAAC CCCGCTCTTA CACATTCCAG CCCTGAAAAA      2640

GGGCATCAAA TTAAACCACA CCTATGGTGT ATGCATTTAT TTGCATACAT TCAATCAATT      2700

GTTATCTAAG GAAATACTTA CATATGCATG ATAAAATTAT TCATCTGACT GATGATTCTT      2760

TTGATACTGA TGTACTTAAG GCAGATGGTG CAATCCTGGT TGATTTCTGG GCACACTGGT      2820

GCGGTCCGTG CAAAATGATC GCTCCGATTC TGGATGAAAT CGCTGACGAA TATCAGGGCA      2880

AACTGACCGT TGCAAAACTG AACATCGATC ACAACCCGGG CACTGCGCCG AAATATGGCA      2940

TCCGTGGTAT CCCGACTCTG CTGCTGTTCA AAAACGGTGA AGTGGCGGCA ACCAAAGTGG      3000

GTGCACTGTC TAAAGGTCAG TTGAAAGAGT TCCTCGACGC TAACCTGGCC GGTTCTGGTT      3060

CTGGTGATGA CGATGACAAA GGTCCACCAC CAGGTCCACC TCGAGTTTCC CCAGACCCTC      3120

GGGCCGAGCT GGACAGCACC GTGCTCCTGA CCCGCTCTCT CCTGGCGGAC ACGCGGCAGC      3180

TGGCTGCACA GCTGAGGGAC AAATTCCCAG CTGACGGGGA CCACAACCTG GATTCCCTGC      3240

CCACCCTGGC CATGAGTGCG GGGGCACTGG GAGCTCTACA GCTCCCAGGT GTGCTGACAA      3300

GGCTGCGAGC GGACCTACTG TCCTACCTGC GGCACGTGCA GTGGCTGCGC GGGGCAGGTG      3360

GCTCTTCCCT GAAGACCCTG GAGCCCGAGC TGGGCACCCT GCAGGCCCGA CTGGACCGGC      3420
```

-continued

```
TGCTGCGCCG GCTGCAGCTC CTGATGTCCC GCCTGGCCCT GCCCCAGCCA CCCCCGGACC      3480

CGCCGGCGCC CCCGCTGGCG CCCCCCTCCT CAGCCTGGGG GGGCATCAGG GCCGCCCACG      3540

CCATCCTGGG GGGGCTGCAC CTGACACTTG ACTGGGCCGT GAGGGGACTG CTGCTGCTGA      3600

AGACTCGGCT GTGAAAGCTT ATCGATACCG TCGACCTGCA GTAATCGTAC AGGGTAGTAC      3660

AAATAAAAAA GGCACGTCAG ATGACGTGCC TTTTTTCTTG TGAGCAGTAA GCTTGGCACT      3720

GGCCGTCGTT TTACAACGTC GTGACTGGGA AAACCCTGGC GTTACCCAAC TTAATCGCCT      3780

TGCAGCACAT CCCCCTTTCG CCAGCTGGCG TAATAGCGAA GAGGCCCGCA CCGATCGCCC      3840

TTCCCAACAG TTGCGCAGCC TGAATGGCGA ATGGCGCCTG ATGCGGTATT TTCTCCTTAC      3900

GCATCTGTGC GGTATTTCAC ACCGCATATA TGGTGCACTC TCAGTACAAT CTGCTCTGAT      3960

GCCGCATAGT TAAGCCAGCC CCGACACCCG CCAACACCCG CTGACGCGCC CTGACGGGCT      4020

TGTCTGCTCC CGGCATCCGC TTACAGACAA GCTGTGACCG TCTCCGGGAG CTGCATGTGT      4080

CAGAGGTTTT CACCGTCATC ACCGAAACGC GCGA                                 4114
```

What is claimed is:

1. An isolated DNA molecule comprising a DNA sequence selected from the group consisting of:
   (a) nucleotides 2599 through 3132 of SEQ ID NO:13, and
   (b) nucleotides encoding amino acids 120 through 296 of SEQ ID NO:14.

2. A nucleic acid vector comprising a DNA according to claim 1.

3. A host cell transformed or transfected with a nucleic acid vector of claim 1.

4. A method for producing IL-11 polypeptide comprising:
   (a) growing, in culture, a host cell of claim 3, and
   (b) isolating from said host cell or said culture the polypeptide product of the expression of said DNA.

5. A purified interleukin-11 (IL-11) protein encoded by a DNA encoding amino acids 120 through 296 of SEQ ID NO:14.

6. A purified IL-11 protien amino acids 120 through 296 of SEQ ID NO:13.

7. A composition comprising an IL-11 protein encoded by a DNA molecule comprising a DNA sequence selected from the group consisting of:
   (a) nucleotides 2599 through 3132 of SEQ ID NO:13, and
   (b) nucleotides encoding amino acids 120 through 296 of SEQ ID NO:14.

* * * * *